United States Patent [19]

Hammesfahr et al.

[11] Patent Number: 5,710,194

[45] Date of Patent: *Jan. 20, 1998

[54] DENTAL COMPOUNDS, COMPOSITIONS, PRODUCTS AND METHODS

[75] Inventors: Paul D. Hammesfahr, Wyoming; Kewang Lu, Dover; Paul A. Silver, Wilmington, all of Del.

[73] Assignee: Dentsply Research & Development Corp., Milford, Del.

[*] Notice: The term of this patent shall not extend beyond the expiration date of Pat. No. 5,338,773.

[21] Appl. No.: 603,957

[22] Filed: Feb. 15, 1996

Related U.S. Application Data

[63] Continuation-in-part of Ser. No. 259,833, Jun. 15, 1994, which is a continuation-in-part of Ser. No. 49,221, Apr. 19, 1993, Pat. No. 5,338,773.

[51] Int. Cl.$^6$ .............................. A61K 6/08; C07C 322/00
[52] U.S. Cl. .................. 523/116; 523/115; 524/433; 524/559; 526/318.1; 526/318.2; 526/334; 562/473; 562/490; 562/495
[58] Field of Search ........................... 523/115, 116; 524/433, 559; 526/318.1, 318.2, 334; 562/473, 490, 495

[56] References Cited

U.S. PATENT DOCUMENTS

| | | | |
|---|---|---|---|
| 3,835,090 | 9/1974 | Gander et al. | 523/116 |
| 4,503,169 | 3/1985 | Randklev | 523/115 |
| 4,540,723 | 9/1985 | Ying | 523/115 |
| 5,171,763 | 12/1992 | Ohno et al. | 523/116 |
| 5,338,773 | 8/1994 | Lu et al. | 523/116 |

*Primary Examiner*—Andrew E. C. Merriam
*Attorney, Agent, or Firm*—Dale R. Lovercheck; James B. Bieber

[57] ABSTRACT

The invention provides polymerizable dental, compounds, compositions, including the compounds and products for mixing the compositions and methods of using the compositions. Aryl acid compounds are provided in accordance with the invention. The compositions include at least one polymerizable aryl acid compound, an effective amount of a polymerization initiator, and at least 10 percent by weight of ceramic, metal and/or metal oxide filler particles having a particle size less than 500 microns. The dental products of the invention include a polymerizable composition in an enclosure having at least two chambers separated by a wall adapted to be ruptured prior to or during mixing of the composition. Compositions of the invention are preferred for use in these enclosures. Core build up material including a polymerizable acid containing compound is used to support dental crowns and adhere them to teeth in accordance with the invention.

23 Claims, 1 Drawing Sheet

DENTAL COMPOUNDS, COMPOSITIONS, PRODUCTS AND METHODS

This is a continuation-in-part of U.S. patent application Ser. No. 08/259,833 filed Jun. 15, 1994 (case 1725), which is a continuation-in-part of U.S. patent application Ser. No. 08/049,221 filed Apr. 19, 1993 (case 1709), which issued Aug. 16, 1994 as U.S. Pat. No. 5,338,773.

TECHNICAL FIELD

The invention relates to dental compounds, compositions, products and methods of use thereof. Compositions of the invention are useful as dental adhesives, pit and fissure sealants, luting cements, liners, bases, restoratives and core build up material.

The invention provides dental compositions which include a polymerizable aryl acid compound and at least 10 percent ceramic, metal and/or metal oxide filler and have less wear and more adhesion to teeth than prior art dental restorative material. The invention provides dental compositions having polymerizable acid compounds within enclosures having a readily rupturable wall. The invention provides novel aryl acid compounds having aryl moieties. The invention provides packable and fluoride releasing restorative compositions with superior adhesion to dentin, enamel and cementum without the need for separate steps of acid etching dental enamel to adhere thereto.

BACKGROUND ART

The prior art does not provide a polymerizable dental composition, which includes one or more polymerizable aryl acid compounds within the scope of formula I; a polymerization initiator; at least 10 percent by weight of ceramic, metal and/or metal oxide filler particles having a particle size less than 500 microns, or products enclosing such compositions and methods of use thereof.

The prior art does not provide a dental product including an enclosure having at least two chambers separated by a wall adapted to be ruptured, and enclosing a polymerizable dental composition including a polymerizable compound and an effective amount of a polymerization initiator and at least 10 percent by weight of ceramic, metal and/or metal oxide filler particles having a particle size less than 500 microns.

It is an object of the invention to provide a polymerizable dental composition which includes one or more polymerizable aryl acid compounds within the scope of formula I, a polymerization initiator at least 10 percent by weight of ceramic, metal and/or metal oxide filler particles having a particle size less than 500 microns, products enclosing such composition and methods of use thereof.

It is an object of the invention to provide a dental product including an enclosure having at least two chambers separated by a wall adapted to be ruptured, and enclosing a polymerizable dental composition including a polymerizable compound and an effective amount of a polymerization initiator and at least 10 percent by weight of ceramic, metal and/or metal oxide filler particles having a particle size less than 500 microns.

"PENTA" as used herein refers to dipentaerythritol pentacrylate phosphoric acid ester which may be prepared according to Example 2 of U.S. Pat. No. 4,816,495.

"OEMA" as used herein refers to the reaction product of 1 mole 4,4' oxydiphthalic anhydride (chemical name: 5,5'-oxybis-1,3-isobenzo furandione) and 2 moles of HEMA.

"ODPA" as used herein refers to 4,4'-oxydiphthalic anhydride.

"HEMA" as used herein refers to 2-hydroxyethylmethacrylate.

"TEGDMA" as used herein refers to triethylene glycol dimethacrylate.

"BHT" as used herein refers to butylated hydroxytoluene.

"bisGMA" as used herein refers to bisphenol A-glycidylmethacrylate.

"CQ" as used herein refers to camphorquinone.

"EDAB" as used herein refers to ethyl 4-dimethylaminobenzoate.

"6-FDMA" as used herein refers to the reaction product of 1 mole of hexafluoroisopropylidene-2,2 bis(phthalic acid anhydride)(6-FDA) and 2 moles of 2-hydroxyethyl methacrylate.

"Monomer" as used herein means monomer or oligomer.

"Packable" as used herein refers to compositions which are packable as disclosed in Dougherty et al. U.S. Pat. No. 4,514,174 particularly at columns 6 and 7 and preferably refers to compositions having resistance values greater than about 175 $g/mm^2$, and more preferably greater than 200 $g/mm^2$.

"Set" as used herein means a polymerizable composition undergoes a change so that it becomes firm, stiff and nonpliable.

As used herein "The MAX Lite" means THE MAX™, a curing unit for light-polymerizable dental materials sold by Dentsply international Inc. through its L. D. Caulk Division.

Throughout this disclosure unless otherwise specified amounts of each component of a composition are in percent by weight.

DISCLOSURE OF INVENTION

The invention provides polymerizable dental, compounds, compositions, including the compounds and products for mixing the compositions and methods of using the compositions. Aryl acid compounds are provided in accordance with the invention. The compositions of the invention include at least one polymerizable aryl acid compound, an effective amount of a polymerization initiator, and at least 10 percent by weight of ceramic, metal and/or metal oxide filler particles having a particle size less than 500 microns. The dental products of the invention include a polymerizable composition in an enclosure having at least two chambers separated by a wall adapted to be ruptured prior to or during mixing of the composition. Compositions of the invention are preferred for use in these enclosures. Core build up material including a polymerizable acid containing compound is used to support dental crowns and adhere them to teeth in accordance with the invention. Compositions of the invention are preferred for use in restoring teeth by replacing missing tooth structure

BEST MODES FOR CARRYING OUT THE INVENTION

Figure 1:
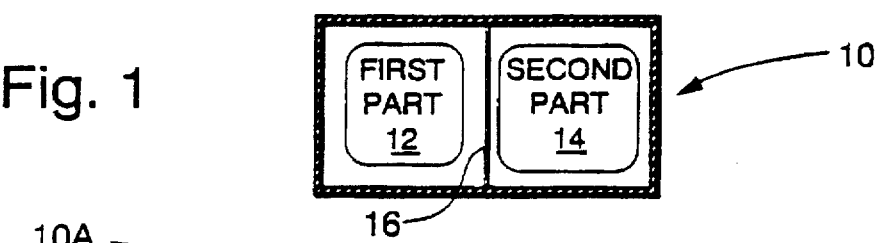
FIG. 1 is a schematic representation of two part composition in a storage and mixing enclosure in accordance with a preferred embodiment of the invention.

Compositions of the invention provide a packable restorative material having superior adhesion to dentin, enamel and bone. In accordance with the invention are provided packable compositions which include at least one a polymerizable compound within the scope of the general formula I, an effective amount of polymerization initiator and at least 10 percent by weight of ceramic, metal or metal oxide filler particles having a particle size less than 500 microns, products enclosing such compositions and methods of use thereof. In order of increasing preference the filler is at least 40, 50, 60, 70, 80 or 90 percent by weight of the composition. These compositions are stable and adapted to not set in order of increasing preference for at least 12 hours, 24 hours, or 36 hours, more preferably for at least 7 days and most preferably for at least 1 year in the absence of polymerization initiation.

Packable dental compositions of a preferred embodiment of the invention include at least one polymerizable unsaturated substituted aromatic acid compound within the scope of the general formula (I):

$$[R']\text{---}[R_1\text{''}\text{---}R_1']_{q_1}\text{---}R\text{''}\text{---}R']_q\text{---}R_1]_{q_2} \quad (I)$$

wherein each R' independently is within the scope of the general formula:

$$R_1\text{-}\underset{Z_1}{\underbrace{\langle\bigcirc\rangle\langle\bigcirc\rangle}}\text{-}X\text{-}\underset{Z_2}{\underbrace{[\langle\bigcirc\rangle\langle\bigcirc\rangle]_n}}_m$$

each $R_1'$ independently is within the scope of the general formula:

$$\underset{Z_1}{\underbrace{\langle\bigcirc\rangle\langle\bigcirc\rangle}}\text{-}X\text{-}\underset{Z_2}{\underbrace{[\langle\bigcirc\rangle\langle\bigcirc\rangle]_n}}_m$$

each $R_1''$ and R" independently is a divalent hydrocarbon group selected from the group consisting of alkyl alkylene having from 2 to 40 carbons, alkylene having from 4 to 40 carbon atoms, aryl alkylene having from 6 to 40 carbon, ether alkylene having from 2 to carbons and alkyl aryl alkylene having from 7 to 40 carbon atoms, each X independently is $$\underset{}{\overset{O}{\underset{\|}{C}}}, \quad O, \quad S, \quad \underset{\underset{\|}{O}}{\overset{O}{\underset{\|}{S}}}, \quad \underset{}{\overset{O}{\underset{\|}{S}}}, \quad \underset{}{\overset{R_9}{\underset{|}{N}}}, \quad \underset{}{\overset{R_{10}}{\underset{|}{P}}}, \quad \underset{R_{11}}{\overset{OR_{13}}{\underset{|}{P}}}, \quad \underset{OR_{14}}{\overset{O}{\underset{\|}{O-P-O}}},$$

$$\underset{R_4}{\overset{R_3}{\underset{|}{-C-}}}, \quad \underset{}{\overset{O}{\underset{\|}{-C-R_{15}-C-}}} \overset{O}{\underset{\|}{}}, \quad (O)_a\text{+}(\underset{R_6}{\overset{R_5}{\underset{|}{C}}})_b\text{---}O\text{-}_p$$

or omitted whereby the adjacent rings are directly covalently bonded together, each $R_1$ independently is a polymerizable unsaturated moiety having from 2 to 30 carbon atoms, $R_3$, $R_4$, $R_5$, and $R_6$ each independently is hydrogen, halogen, alkyl having from 1 to 10 carbon atoms or having alkyl of from 1 to 10 carbon atoms, $R_9$, $R_{10}$, $R_{11}$, $R_{12}$, $R_{13}$ and $R_{14}$ each independently is hydrogen, alkyl having from 1 to 10 carbon atoms or aryl having from 6 to 10 carbon atoms, $R_5$ is alkylen diol, alkylene diamine, substituted alkylene diol or substituted alkylene diamine, preferably $R_{15}$ is $$-OCH_2-\underset{}{\overset{OH}{\underset{|}{CH}}}-CH_2O-$$

$Z_1$ and $Z_2$ each independently is a moiety including an acid group, a, m and n each independently is 0 or 1, b, and p independently is an integer from 1 to 10, q is zero or 1, $q_1$ is zero, 1 or 2, $q_2$ is zero or 1, when q is zero, $q_2$ is 1; and when q is 1 $q_2$ is zero.

Compounds within the scope of general formula I wherein at least one of q and $q_1$ is greater than zero provide new, useful, nonobvious abrasion resistant dental material having adhesion to dentin of at least 300 psi.

In accordance with a preferred embodiment of the invention $R_1$ and $R_2$ each independently is:

$$\underset{}{\overset{O}{\underset{\|}{-C-R_7-O-C-}}}\overset{O}{\underset{\|}{}}\underset{R_8}{\overset{}{\underset{|}{C}}}=CH_2$$

wherein $R_7$ is a divalent carbon containing radical and $R_8$ is hydrogen, halogen or alkyl having from 1 to 10 carbon atoms.

Exemplary of R" are $$-CH_2\text{-}\langle\bigcirc\rangle\text{-}CH_2-$$

$$-CH_2-\langle\bigcirc\rangle-CH_2-$$

$$-CH_2CH_2OCH_2CH_2-$$

$$-CH_2CH_2OCH_2CH_2O-\langle\bigcirc\rangle-\underset{CH_3}{\overset{CH_3}{\underset{|}{C}}}-\langle\bigcirc\rangle-OCH_2CH_2OCH_2CH_2-$$

and

-continued

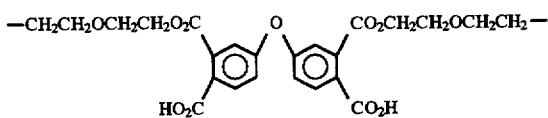

In a preferred embodiment of the invention compounds are provided within the scope of general formula I wherein n and m are zero, X is oxygen, sulfonyl or bis (trifluoromethyl)methyl; and $R_1$ is

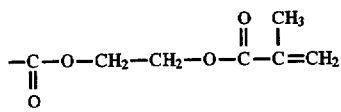

Most preferably compounds within the scope of general formula I are those wherein X is oxygen or bis (trifluoromethyl)methyl. Preferred polymerizable unsaturated groups $R_1$ each independently is alkenyl, alkenoxy, cycloalkenyl, arylalkenyl, and alkenaryl moieties; with vinyl, and styryl moieties being more preferred, and acryl and methacryl moieties that constitute the polymerizable groups of many monomers in dental materials being especially preferred. Exemplary $R_1$ (meth)acrylate moieties include:

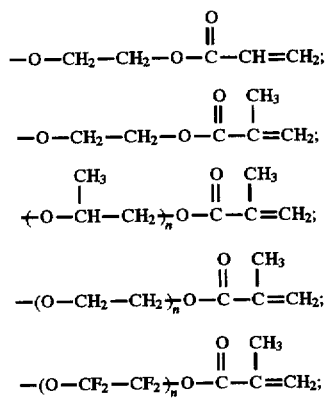

where n preferably is an integer from 1 to 10. Preferably $R_1$ is (meth)acryloyloxyethyl moieties.

Preferably these compositions are mixed with monomers and/or prepolymers and applied to a tooth.

Compounds within the scope of general formulas I, preferably have molecular weights less than 100,000; more preferably less than 20,000 and most preferably less than 5,000 and especially preferred are those having molecular weights less than 1,000.

Particulate material for use in compositions in accordance with the invention preferably have a particle size having a longest dimension in order of increasing preference of: less than 1 mm, less than 0.1 mm, less than 0.01 mm or less than 0.001 mm.

Preferred compounds within the scope of formula I include diesters which are the adducts of 2,2-bis(3,4-dicarboxylphenyl)hexafluoropropane anhydride, 4,4'-oxydiphthalic anhydride, 4,4'-sulfonyldiphthalic anhydride, respectively with 2-hydroxyethyl methacrylate. In a preferred embodiment at least two aromatic rings of a compound within the scope of formula I are joined through at least one saturated carbon, oxygen or sulfonyl.

Aromatic dianhydrides preferred for making compounds for use in complexes within the scope of general formula I react to form partial esters and carboxylic acid functionality. Dianhydrides having at least two aromatic rings are more preferred. Most preferably at least two aromatic rings are joined as shown in formula I to provide disruption of conjugation between the aromatic rings. Most preferred examples are 4,4'-oxydiphthalic anhydride and 2,2-bis(3,4-dicarboxyphenyl)hexafluoropropane dianhydride.

Preferably the polymerizable initiator promotes free radical polymerization and preferably includes a visible light curing and/or a redox catalyst system. Preferably the composition includes liquid diluent monomers. Diluent monomers preferably co-polymerize with the polymerizable monomer within the scope of general formula I. Suitable polymerizable co-monomers are disclosed in U.S. Pat. No. 4,657,941 particularly at column 3 line 5 through column 5 line 59 and U.S. Pat. No. 4,514,342 both of which are incorporated herein by reference. Exemplary fillers include metals, metal oxides, silica, silicates, alumina, aluminates, calcium fluoride, strontium fluoride, glasses including fluorine glasses, ceramics and minerals including mica, zeolites, ceramics, calcium apatites, silane and/or silanol treated filler and organic polymers and those disclosed in U.S. Pat. Nos. 4,758,612 and 5,079,277.

A preferred composition of the invention includes a monomer compound within the scope of general formula I, at least one finely divided filler and curing agent.

A dental composition in accordance with the invention preferably includes a compound of general formula I, initiator and filler. Dental cements and dental filling compositions in accordance with a preferred embodiment of the invention include monomer compounds within the scope of general formula I.

The compounds within the scope of general formula I have at least two different functional substituent groups, one of which is capable of addition polymerization and the other of which is carboxyl or other acid or reactive acid derivative. Most preferably these compounds include at least one polymerizable group and one or more acid or reactive acid derivative groups. Preferred compounds within the scope of general formula I are derived acid formed from the reaction of 4,4'-oxydiphthalic anhydride or 2,2-bis(3,4-dicarboxylphenyl)hexafluorpropane dianhydrides with a polymerizable hydroxyl or polyhydric compound to form esters and partial esters thereof.

The carboxyl group itself is most preferred over other acid moieties or the reactive acid derivative ions. Especially appropriate acid moieties are all those that react with oxicidic, mineral, ceramic, vitreous, or metallic fillers.

Examples of these other acid moieties include:

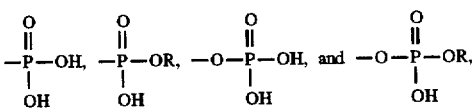

of phosphorus acids wherein R is alkyl, aryl, or vinyl; the moieties —$SO_2H$, $SO_3H$, or —O—$SO_3H$ of sulfuric acids; the moieties:

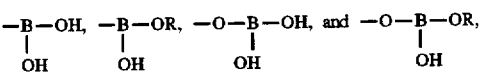

of boron acids wherein R is alkyl, aryl, or vinyl and cationic acid moieties including —$NR_2H+$ wherein R is H or alkyl. The reactive acid derivatives can be substituted with acid halides, with acid anhydrides, and with acid amides, nitriles, and esters that readily hydrolyze into acid, such as can enter into ion-exchange, neutralization, salt formation, or chelation reactions with the reactive filler. Preferred acid or reactive acid derivatives are carboxylate, phosphate, phosphonate, sulfonate, or borate acid moieties and/or of their reactive derivatives.

The compositions of the invention are formulated as one, two or more components, visible light curable, self cure, and/or dual cure product or combinations of these. The composition of a preferred embodiment of the invention includes polymerizable carboxylic acid monomer, an optional filler and/or diluent, a cationic elutable glass or other source of polyvalent cations, and a polymerization catalyst system.

A method of producing the ethylenically unsaturated carboxylic compounds is disclosed in Dentsply's U.S. Pat. No. 5,338,773 at columns 10 and 11, which provides as follows:

In the presence of acid, base or other suitable catalyst one mole 4,4'-oxydiphthalic anhydride is reacted with two moles of a compound of the general formula R—OH, wherein R is a polymerizable unsaturated moiety having from 2 to 30 carbon atoms. This yields a liquid product which is believed to be a mixture of isomer monomers of general formulas II–IV:

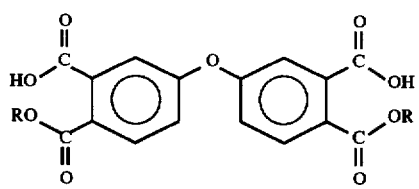

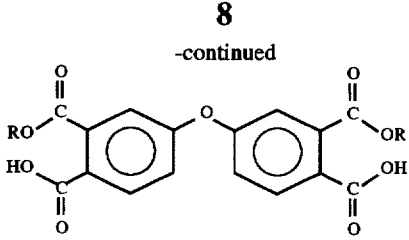

and

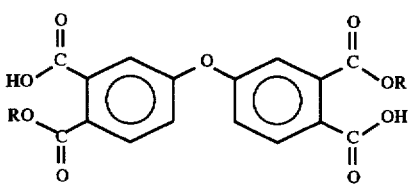

By reacting one mole of oxydiphthalic anhydride with two moles of methacryloyloxyethyl alcohol also known as 2-hydroxyethyl methacrylate (HEMA) in the presence of catalyst a liquid product is formed which is believed to be a mixture of isomer monomers V–VII:

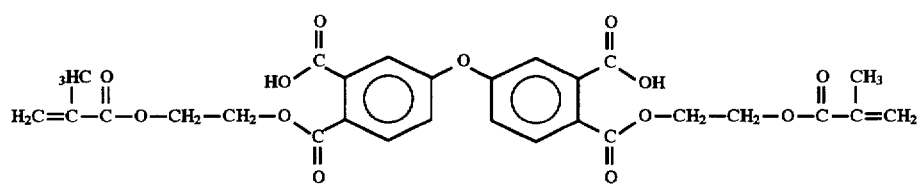

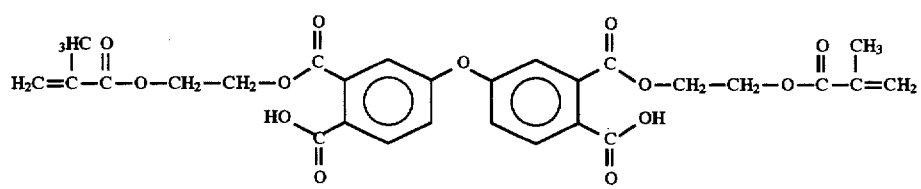

and

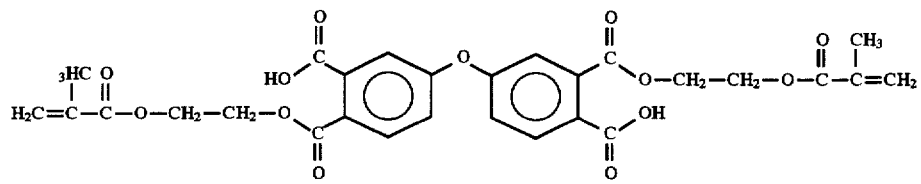

Monomer compounds within the scope of general formula I are reactive esters which have at least one unreacted carboxylic acid group and one polymerizable group in the monomer. The number of reacted or unreacted carboxylic acid groups in the monomer is controlled by varying the reaction conditions and molar ratio of reactants. The monomer compounds of the invention polymerize by addition polymerization through the ethylenically unsaturated group. Curing agents, catalysts, initiators and/or accelerators, are used to expedite and control the polymerization. A peroxide initiator, for example benzoyl peroxide, and/or heat are useful to initiate the reaction. Accelerators enhance the reaction so that it may proceed more expeditiously at room temperature. Accelerators preferably include reducing agents such as amines or sulfinates, and/or transition metal ions. Ultraviolet and/or visible light may be used with initiators and accelerators to initiate and accelerate the polymerization. Visible light curing is preferred for curing the compositions of the invention in the mouth.

For preformed objects, or those cured outside the body, other forms of radiation, for example ultraviolet ionizing radiation and light from a laser source, are preferred for curing the compositions of the invention.

In accordance with the method of the invention in-vivo polymerization does not harm the patient within whom polymerization of monomer compound within the scope of general formula I occurs. To initiate by irradiation with ultraviolet or visible light the initiator, for example a benzophenone or camphorquinone is preferably used to form a single, ready to use shelf-stable composition. A preferred embodiment of the composition of the invention includes a polymerization catalyst system having a light sensitive polymerization initiator such as camphorquinone, a reducing agent such as ethyl 4-dimethylaminobenzoate (EDAB) and an oxidizing agent such as benzoyl peroxide.

Redox polymerization systems known to the art are preferably used to polymerize the composition of the invention. Preferred redox polymerization catalyst systems for use in accordance with the invention include, a peroxide and tributyl boron and/or a transition metal salt. Redox polymerization catalysts and catalyst systems are those disclosed in U.S. Pat. No. 4,657,941 at column 7 line 10 through column 8 line 27 incorporated herein by reference. A particular polymerization method and system may be preferred depending on the application requirements of the material. For example a CAA/AP/BPO system.

Fillers which are especially suited for use in compositions of the invention are inorganic glasses such as are used in glass ionomer cements. Exemplary of such fillers are those of U.S. Pat. No. 4,814,362 which is incorporated herein by reference in its entirety. Preferred fillers are glasses formed from or including, barium, calcium, strontium, lanthanum, tantalum, and/or tungsten silicates and aluminates and/or aluminosilicates, silica, including submicron silica, quartz, and/or ceramics for example, calcium hydroxy apatite. In a preferred embodiment of the invention reactive cations, especially those of calcium, strontium and aluminum, and anions especially fluoride ions; are eluted from the fillers. The fillers used in the invention preferably are reduced in particle size and in a preferred embodiment are silanated before they are incorporated into such compositions. Preferred levels of filler are from about 20% to about 85% based on the total weight of the cement composition, with from about 40% to about 85% being more preferable and about 50-80% being most preferred. If a more finely particulated filler is used, amounts of filler may be decreased due to the relative increase in surface area which attends the smaller sizes of particles. Preferred particle size distributions are from 0.02 to 50 microns, more preferably 0.1 to 10 microns, and most preferably 1 to 6 microns.

In a preferred embodiment compositions of the invention include solvents, plasticizers, pigments, anti-microbials and therapeutics which may be time released from the composition, and oxidation inhibitors such as butylated hydroxytoluene. In addition to compounds within the scope of general formula I compositions in accordance with the invention preferably include polymerizable unsaturated diluent monomers, oligomers and/or prepolymers that may also contain any acid groups and/or salts thereof and/or reactive readily hydrolyzing acid-derivative groups thereof. One such preferred monomer is hydroxyalkyl methacrylates. Compositions of the invention may also preferably include compounds having acid groups and/or their salts and/or their readily reactive hydrolyzing derivative groups but do not contain any groups that are unsaturated and polymerizable, such as multi-basic acids or their reactive, readily hydrolyzing derivatives.

In a preferred embodiment of the invention is provided a dental crown product, including a dental crown, supported by core build up material comprising a polymerizable dental composition, comprising: a polymerizable acid compound an effective amount of a polymerization initiator, and at least 10 percent by weight of ceramic, metal and/or metal oxide filler particles having a particle size less than 500 microns. The composition is preferably enclosed by an enclosure, and/or useful as a core build up material which preferably adheres to dentin with an adhesive bond strength of at least 300 psi, more preferably at least 400 psi and most preferably at least 500 psi.

Compounds that have chelating groups but do not contain carboxylic acid groups or readily hydrolyzing acid-derivative groups are preferably included in composition in accordance with the invention, for example vanillates, syringates, and salicylates.

Mixing the compositions of the present invention may be achieved using standard compounding techniques.

FILLING COMPOSITIONS

A preferred dental treatment in accordance with the invention is the application of dental filling compositions which include a curing agent and at least one salt compound within the scope of general formula I. Preferably the dental filling composition includes finely divided reactive filler that can react ionically with the acids or acid derivatives of the monomer.

In accordance with the method of the invention, restorative compositions include at least one polymerizable acid reactive ethylenically unsaturated compound within the scope of general formula I. Such compositions are applied to tooth without prior etching of the tooth.

Preferably, packable restorative compositions in accordance with the invention include more than 80 percent by weight, more preferably more than 90 percent by weight, and most preferably, more than 92 percent by weight metal, metal oxide and/or ceramic particles.

The methods of measurement of compressive strength, transverse flexural strength, diametral tensile strength, bond strength to dentin and fluoride release-static extraction used herein for testing compositions of the invention, particularly those compositions set forth in the following Examples are disclosed in Dentsply's U.S. Pat. No. 5,338,773 at column 14, lines 38–68 and column 15, lines 1–68.

WEAR

The average relative wear loss used herein is a unitless comparative value. For example a sample having an average relative wear loss of 2 has twice the loss of volume due to wear under the same conditions as a sample having an average relative wear loss of 1.

Having generally described the invention, a more complete understanding can be obtained with reference to certain specific examples, which are included for purposes of illustration only. It should be understood that the invention is not limited to the specific details of the Examples.

PREPARATION OF ACID MONOMERS

6-FDMA is the reaction product of 1 mole of hexafluoroisopropylidene-2,2 bis(phthalic acid anhydride) and 2 moles of 2-hydroxyethyl methacrylate, (identified hereafter as HEMA) as disclosed in Example 1 of Dentsply's U.S. Pat. No. 5,338,773.

SYNTHESIS OF BTDMA

BTDMA is the reaction product of 1 mole of 3,3',4,4'-benzophenone tetracarboxylic acid dianhydride and 2 moles 2-hydroxyethyl methacrylate. When prepared in an excess of 2-hydroxyethyl methacrylate the HEMA serves as a solvent for the esterification reaction as disclosed in Example 2 of Dentsply's U.S. Pat. No. 5,338,773.

SYNTHESIS OF OEMA

OEMA is the reaction product of 1 mole 4,4'-oxydiphthalic anhydride (chemical name: 5,5'-oxybis-1,3-isobenzo furandione) and 2 moles of HEMA as disclosed in Example 3 of Dentsply's U.S. Pat. No. 5,338,773.

SYNTHESIS OF OPMA

OPMA is the reaction product of 1 mole oxydiphthalic anhydride and 2 moles of HPMA as disclosed in Example 4 of Dentsply's U.S. Pat. No. 5,338,773.

PREPARATION OF STDMA

STDMA is the reaction product of 1 mole of 4,4'-sulfonyldiphthalic dianhydride (STDA) and 2 moles of HEMA. In this example STDMA is prepared in an excess of HEMA as disclosed in Example 5 of Dentsply's U.S. Pat. No. 5,338,773.

PREPARATION OF OEMA IN TEGMA

OEMA is the reaction product of 1 mole of oxydiphthalic dianhydride (ODPA) and 2 moles of HEMA as disclosed in Example 6 of Dentsply's U.S. Pat. No. 5,338,773.

PREPARATION OF POWDERS

Strontium aluminofluorosilicate glass powder used in Examples 27B is made by fusing aluminum oxide, silica, strontium fluoride, aluminum fluoride, aluminum phosphate, and cryolite according to procedures disclosed in U.S. Pat. No. 4,814,362 to form particles which are milled to a mean particle size of 5.5 microns. It has the following analysis with all elements except fluorine being calculated as the oxide of the element:

The composition of strontium aluminofluorosilicate glass particles used herein is as follows:

|  | Parts by weight |
|---|---|
| $Al_2O_3$ | 24.6 |
| $SiO_2$ | 32.1 |
| $Na_2O$ | 2.9 |
| SrO | 28.7 |
| F | 12.3 |
| $P_2O_5$ | 4.8 |

The barium aluminofluorosilicate glass particles used in Examples 18, 19, 20, 22–27, 27A and 27C are 7726 glass sold by Corning. It is preferably formed as disclosed in Danielson U.S. Pat. No. 4,920,082.

SYNTHESIS OF GMA

In a 500 mL round bottom flask is placed 17.1 g (0.15 mole) glutaric anhydride, 20.1 g (0.155 mole) HEMA, 2.2 g (0.15 mole) 4pyrrolidino-pyridine and 15.2 g (0.15 mole) triethylamine in 300 mL methylene chloride. The solution is stirred overnight. IR analysis indicated no anhydride remained.

The solution is washed with 250 mL 2N hydrochloric acid, then twice with 200 mL portions of deionized water. The washed solution is dried over anhydrous sodium sulfate and the solvent stripped under vacuum to obtain a liquid product

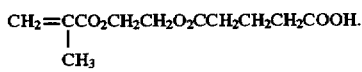

SYNTHESIS OF SMA

In a 500 mL round bottom flask is placed 15.0 g (0.15 mole) succinic anhydride, 21.5 g (0.165 mole) HEMA, 2.22 g (0.015 mole) 4-pyrrolidino pyridine and 15.2 g (0.15 mole) triethyl amine in 300 mL methylene chloride. The solution is stirred overnight.

The solution is washed with 200 mL 2N hydrochloric acid, then twice with 200 mL deionized water. The washed solution is dried over anhydrous sodium sulfate and the solvent stripped under vacuum to give a liquid product.

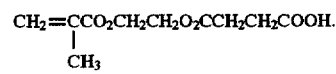

SYNTHESIS OF OEMA/GMA RESIN 31.0 grams (0.1 mole) 4,4-oxydiphthalic anhydride (ODPA), 11.4 grams of glutaric anhydride (0.1 mole), 39.0 grams of hydroxyethyl methacrylate (HEMA), (0.30 mole), and 0.05 grams of butylated hydroxytoluene are reacted at room temperature for 30 minutes followed by stirring at 110° C. for 2.0 hours to form a very viscous mixture of the adduct of ODPA and HEMA (OEMA) and an adduct of glutaric anhydride and HEMA (GMA). Alternatively, OEMA may be prepared from ODPA (0.1 mole) and HEMA (0.2 mole) in GMA prepared as described above.

SYNTHESIS OF 6-FDMA/PMA RESIN ADDUCTS WITH HEMA 39.0 grams of HEMA, 0.06 g butylated hydroxytoluene, and 14.8 grams of phthalic anhydride are reacted at 100°–110° C. for 60 minutes. Then 44.4 grams of hexafluoroisopropylidene-2,2-bis(phthalic acid anhydride) (6-FDPA) is added and stirred at between 120° and 130° C. for 4.0 hours to form a clear, slightly yellow resin, mixture of 6-FDMA and an adduct of phthalic anhydride and HEMA (PMA).

SYNTHESIS OF 6-FDMA/GMA RESIN:

39.0 grams (0.30 mole) hydroxyethylmethacrylate, 44.4 grams of hexafluoroisopropylidene-2,2-bis(phthalic acid anhydride), (6-FDPA, 0.1 mole) 11.4 grams of glutaric anhydride (0.1 mole) and 0.06 grams of butylated hydroxytoluene are reacted at 100° C. for 4.0 hours to form a viscous slightly yellow clean resin, mixture of 6-FDMA and an adduct of glutaric anhydride and HEMA (GMA). Alternatively, 6-FDMA/GMA may be prepared by reacting 6-FDPA (0.1 mole) with HEMA (0.2 moles) in GMA prepared as described above.

EXAMPLE A

SYNTHESIS of OEMAMA:

In a 500 mL round bottom flask is placed 15.50 g (0.05 mole) 4,4'-oxydiphthalic anhydride (ODPA), 24.86 g (0.11 mole) glyceryl dimethacrylate, 1.48 g 4-pyrrolidino pyridine and 10.10 g (0.10 mole) triethyl amine (TEA) in 300 mL methylene chloride. On addition of TEA, the solids dissolved. The solution is stirred overnight.

The solution is washed twice with 200 mL 2N hydrochloric acid and twice with 200 mL deionized water. A saturated salt solution (150 mL) is used to break an emulsion during the second washing. The solution is dried over anhydrous sodium sulfate and the solvent removed under vacuum to give OEMAMA a light yellow resin, having structural formula:

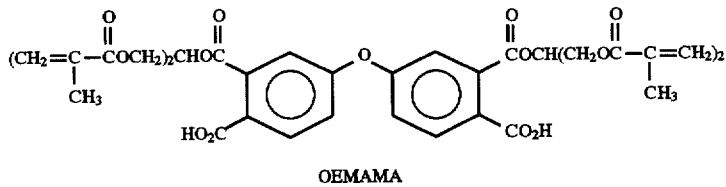

OEMAMA

EXAMPLE 1

A two component metallic oxide containing composition is formed by mixing 44.8 grams of OEMA, 4.1 grams of water; 30 grams of triethylene glycol dimethacrylate (TEGDMA); 19.4 grams of hydroxyethyl methacrylate (HEMA); 0.6 grams of ethyl-4-dimethylaminobenzoate (EDAB); 0.2 grams camphorquinone, 0.1 grams of butylated hydroxytoluene; 1.0 gram of Uvinol M-40; to form a polymerizable liquid. 1 parts of this polymerizable liquid is mixed with 1.5 parts of powder. The powder is made up of 10 parts by weight silanated aluminum oxide and 0.1 parts by weight of initiator. The initiator is made by mixing 10 parts of benzoyl peroxide (BPO), 0.2 parts by weight of cupric acetylacetonate (CAA) and 1.5 parts by weight of ascorbyl palmitate (AP). The liquid and powder are enclosed in a plastic mixing capsule. The capsule is placed in an actuator, and the actuator is operated to vibrate the capsule for about 10 seconds and the powder and liquid are mixed during the actuation to form a paste. The paste hardens in three minutes to form a set polymeric metallic oxide containing material having a flexural strength of 87 MPa; a flexural modulus of 5138 MPa; and compressive strength of 210 MPa.

EXAMPLE 2

The procedure of Example 1 is followed except that aluminum oxide, which is not silanated, is used in place of silanated aluminum oxide to form polymeric metallic oxide containing material having a flexural strength of 50 MPa, a flexural modulus of 5206 MPa; and a compressive strength of 185 MPa.

EXAMPLE 3

A two component composition is formed by mixing 44.8 grams of OEMA, 4.1 grams of water; 30 grams of triethylene glycol dimethacrylate (TEGDMA); 19.4 grams of hydroxyethyl methacrylate (HEMA); 0.6 grams of ethyl-4-dimethylaminobenzoate (EDAB); 0.2 grams camphorquinone, 0.1 grams of butylated hydroxytoluene; 1.0 gram of Uvinol M-40; to form a polymerizable liquid. 1 parts of this polymerizable liquid is mixed with 1.5 parts of powder. The powder is made up of 10 parts by weight silanated titanium oxide, having a particle size less than 3 microns, and 0.1 parts by weight of initiator. The initiator is made by mixing 10 parts of benzoyl peroxide (BPO), 0.2 parts by weight of cupric acetylacetonate (CAA) and 1.5 parts by weight of ascorbyl palmitate. The liquid and powder are enclosed in a plastic mixing capsule. The capsule is placed in an actuator, the actuator is operated for about 5 seconds and the powder and liquid are mixed during the actuation to form a paste. The paste hardens to form a set polymeric metallic oxide containing material having a flexural strength of 34 MPa; a flexural modulus of 4674 MPa; and compressive strength of 200 MPa.

EXAMPLE 4

The procedure of Example 3 is followed except that titanium oxide, which is not silanated is used in place of silanated titanium oxide to form polymeric material having a flexural strength of 37 MPa, a flexural modulus of 3730; and a compressive strength of 195 MPa.

EXAMPLE 5

A two component mercury free amalgam paste composition is formed by mixing 44.8 grams of OEMA, 4.1 grams of water; 30 grams of triethylene glycol dimethacrylate (TEGDMA); 19.4 grams of hydroxyethyl methacrylate (HEMA); 0.6 grams of ethyl-4-dimethylaminobenzoate (EDAB); 0.2 grams camphorquinone, 0.1 grams of butylated hydroxytoluene; 1.0 gram of Uvinol M-40; to form a polymerizable liquid. 1.0 parts of this polymerizable liquid is mixed with 2.0 parts of powder. The powder is made up of 10 parts by weight silanated zirconium oxide and 0.1 parts by weight of initiator. The initiator is made by mixing 10 parts of benzoyl peroxide (BPO), 0.2 parts by weight of cupric acetylacetonate (CAA) and 1.5 parts by weight of ascorbyl palmitate. The liquid and powder are enclosed in a plastic mixing capsule. The capsule is placed in an actuator, and the actuator is operated for about 10 seconds and the powder and liquid are mixed during the actuation to form a paste. The paste hardens within three minutes to form a set polymeric metallic oxide containing material having a flexural strength of 61 MPa; a flexural modulus of 2826 MPa; and compressive strength of 221 MPa.

EXAMPLE 6

The procedure of Example 5 is followed except that zirconium oxide, which is not silanated is used in place of silanated aluminum oxide to form polymeric metallic oxide containing material having a flexural strength of 56 MPa, a flexural modulus of 5362 MPa; and a compressive strength of 201 MPa.

EXAMPLE 7

The procedure of Example 5 is followed except that yttrium oxide, which is silanated is used in place of silanated zirconium oxide to form polymeric material having a flexural strength of 58.9 MPa, a flexural modulus of 5342 MPa; and a compressive strength of 176 MPa.

EXAMPLE 8

The procedure of Example 7 is followed except that yttrium oxide, which is not silanated is used in place of silanated yttrium oxide to form polymeric material having a flexural strength of 64 MPa, a flexural modulus of 5034 MPa; and a compressive strength of 155 MPa.

EXAMPLE 9

The procedure of Example 5 is followed except that silanated aluminum oxide is used in place of silanated zirconium oxide with 1 part polymerizable liquid mixed with 2 parts of powder, to form a polymeric metallic oxide containing material having a flexural strength of 81 MPa, a flexural modulus of 7500 MPa and a compressive strength of 261 MPa.

EXAMPLE 10

The procedure of Example 6 is followed except that unsilanated aluminum oxide using 1 part polymerizable liquid mixed with 2 parts powder is used in place of silanated zirconium oxide to form a polymeric material having a flexural strength of 70 MPa, a flexural modulus of 6432 MPa and a compressive strength of 199 MPa.

EXAMPLE 11

The procedure of Example 5 is followed except that silanated silicon carbide is used in place of silanated zirconium oxide, to form a polymeric material having a flexural strength of 79 MPa, a flexural modulus of 10,400 MPa and a compressive strength of 177 MPa.

EXAMPLE 12

The procedure of Example 6 is followed except that unsilanated silicon carbide is used in place of unsilanated zirconium oxide to form a polymeric material having a flexural strength of 51 MPa, a flexural modulus of 9397 MPa and a compressive strength of 128 MPa.

EXAMPLE 13

A two component mercury free, metallic silver composite paste composition is formed by mixing 44.8 grams of OEMA, 4.1 grams of water; 30 grams of triethylene glycol dimethacrylate (TEGDMA); 19.4 grams of hydroxyethyl methacrylate (HEMA); 0.6 grams of ethyl-4-dimethylaminobenzoate (EDAB); 0.2 grams camphorquinone, 0.1 grams of butylated hydroxytoluene; 1.0 gram of Uvinol M-40; to form a polymerizable liquid. 1 part of this polymerizable liquid is mixed with 10 parts of silver metal powder. The metal powder is made up of 10 parts by weight silver powder and 0.1 parts by weight of initiator. The initiator is made by mixing 10 parts of benzoyl peroxide (BPO), 0.2 parts by weight of cupric acetylacetonate (CAA) and 1.5 parts by weight of ascorbyl palmitate. The liquid and powder are enclosed in a plastic mixing capsule. The capsule is placed in an actuator, and the actuator is operated for about 10 seconds and the powder and liquid are mixed during the actuation to form a paste. The paste hardens to form a set polymeric metallic silver composite material having a flexural strength of 41.8 MPa; and a flexural modulus of 4946 MPa.

EXAMPLE 14

The procedure of Example 13 is followed except that a silver-tin alloy (80 percent by weight silver and 20 percent tin) is used in place of silver powder to form polymeric material having a flexural strength of 36 MPa, a flexural modulus of 4689 MPa; and a compressive strength of 89 MPa.

EXAMPLE 15

The procedure of Example 13 is followed except that a mixture of silicon carbide and a metallic dental alloy powder (Dispersalloy™) in a one to one by weight ratio is used in place of silver to form polymeric material having a flexural strength of 57.3 MPa, a flexural modulus of 9379 MPa.

EXAMPLE 16

Powder A, shown in Table 2, and liquid A, shown in Table 3, are mixed in a ratio of 6.5 to 1, as described in Example 1 and shown in Table 1. Powder A is made by mixing 20.5 parts by weight of a metallic dental alloy, 0.6 parts by weight of $SnF_2$, 20.5 parts by weight of barium boro aluminosilicate glass, and 0.4 parts by weight of an initiator composition. The metallic alloy is a mixture of spherical and irregular particles having an approximate composition of 69.3 percent by weight silver, 17.9 percent by weight tin, 11.8 percent by weight copper and 0.9 percent by weight zinc, sold commercially as Dispersalloy™ by Dentsply International, Inc. The initiator composition is 10 parts by weight of benzoyl peroxide, 0.2 parts by weight of copper acetylacetonate and 3.5 parts by weight of ascorbyl palmitate. Liquid A is 16 percent by weight PENTA, 37.926 percent by weight OEMA, 16.254 percent by weight HEMA, 25.20 percent by weight TEGDMA, 4.536 percent by weight water, and 0.084 percent by weight BHT.

The powder-liquid mixture formed polymerizes to form a polymeric material having a compressive strength of 228 MPa, a flexural strength of 109 MPa, a flexural modulus of 11,134 MPa, adhesion to dentin without priming of 792 psi, adhesion to dentin with priming using Prime and Bond (™) [a primer/adhesive sold by Dentsply International, Inc.] of 1272 psi and a wear of 37.1 using an in vitro wear testing device on a polished sample of the polymeric material fixed under a wear testing stylus immersed in an aqueous slurry of polymeric beads. The stylus presses against the polymeric material and then rotates about 30° during each wear cycle. The wear test is complete after 250,000 wear cycles. The polymeric material formed releases fluoride. The cumulative six week static fluoride release is 549 μg/gm.

EXAMPLE 17

Powder B and liquid A are mixed in a ratio of 6.5 to 1, as described in Example 1 and as shown in Table 1. Powder B is made by mixing 7.8 part by weight silver (Ag) powder, 7.8 part by weight barium boro alumino fluoride silicate glass, and 0.08 part by weight initiator composition. The initiator composition is 10 parts by weight of benzoyl peroxide, 0.2 parts by weight of copper acetylacetonate and 3.5 parts by weight of ascorbyl palmitate. Liquid A is 16 percent by weight PENTA, 37.926 percent by weight OEMA, 16.254 percent by weight HEMA, 25.20 percent by weight TEGDMA, 4.536 percent by weight water, and 0.084 percent by weight BHT. The powder-liquid mixture formed polymerizes to form a polymeric material having a compressive strength of 81 MPa, a flexural strength of 22 MPa and a flexural modulus of 3,885 MPa.

EXAMPLE 18

Powder C and liquid A are mixed in a ratio of 6.5 to 1, as described in Example 1 and as shown in Table 1. Powder C is made by mixing 50 parts by weight of a metallic dental alloy and 50 parts by weight barium boro alumino fluoride silicate glass and 1 part by weight initiator composition. The alloy is a mixture of spherical and irregular particles having an approximate composition of 69.3 percent by weight silver, 17.9 percent by weight tin, 11.8 percent by weight copper and 0.9 percent by weight zinc, and is sold commercially as Dispersalloy™ by Dentsply international, Inc. The initiator composition is 10 parts by weight of benzoyl peroxide, 0.2 parts by weight of copper acetylacetonate and 3.5 parts by weight of ascorbyl palmitate. Liquid A is 16 percent by weight PENTA, 37.926 percent by weight OEMA, 16.254 percent by weight HEMA, 25.20 percent by weight TEGDMA, 4.536 percent by weight water, and 0.084 percent by weight BHT. The powder-liquid mixture formed polymerizes to form a polymeric material having a compressive strength of 246 MPa, a flexural strength of 98 MPa, a flexural modulus of 14,810 MPa, adhesion to dentin without priming of 697 psi, an adhesion to dentin with priming using Prime and Bond (™) [a primer/adhesive sold by Dentsply International, Inc.] is 1,426 psi.

The polymeric material formed releases fluoride. The cumulative six week static fluoride release is 561 micrograms of fluoride per gram of polymeric material (μg/gm).

EXAMPLE 19

Powder J and a liquid A are mixed in a ratio of 7.0 to 1 as described in Example 1 and as shown in Table 1. Powder J is made by mixing 10 parts by weight of a metallic alloy powder, (which is a mixture of spherical and irregular particles having an approximate composition of 69.3 percent by weight silver, 17.9 percent by weight tin, 11.8 percent by weight copper and 0.9 percent by weight zinc alloy and sold commercially as Dispersalloy by Dentsply International Inc.), 4 parts by weight barium boro alumino silicate glass and 0.1 part by weight initiator composition. The initiator composition is 10 parts by weight of benzoyl peroxide, 0.2 parts by weight of copper acetylacetonate and 3.5 parts by weight of ascorbyl palmitate. Liquid A is 16 percent by weight PENTA, 37.926 percent by weight OEMA, 16.254 percent by weight HEMA, 25.20 percent by weight TEGDMA, 4.536 percent by weight water, and 0.084 percent by weight BHT. The powder-liquid mixture formed polymerizes to form a polymeric material having a flexural strength of 80.1 MPa, a flexural modulus of 10,833 MPa, and compressive strength of 214 MPa.

EXAMPLE 20

Powder C and liquid B are mixed in a ratio of 6.5 to 1, as described in Example 1 and as shown in Table 1. Powder C is made by mixing 50 parts by weight of a mixture of alloy silver/tin/copper/zinc, 50 parts by weight barium boro alumino fluoride silicate glass and 1 part by weight initiator composition and 1 percent initiator. The mixture of alloy is 69.3 percent by weight silver, 17.9 percent by weight tin, 11.8 percent by weight copper and 0.9 percent by weight zinc, sold commercially as Dispersalloy™ by Dentsply International, Inc. The initiator composition is 10 parts by weight of benzoyl peroxide, 0.2 parts by weight of copper acetylacetonate and 3.5 parts by weight of ascorbyl palmitate. Liquid B is 35.6 percent by weight compound VIIIA made as describe in Example 28, 35.6 percent by weight TEGDMA, 23.9 percent by weight HEMA and 4.9 percent by weight H₂O. The powder-liquid mixture formed polymerizes to form a polymeric material having a flexural strength of 49 MPa, a flexural modulus of 6,562 MPa.

EXAMPLE 21

Powder D and liquid D are mixed in a ratio of 6.5 to 1, as shown in Table 1. The powder is made by mixing 50 parts by weight of a metallic dental mixture of alloy powder, 50 parts by weight barium boro alumino silicate glass and 1 part by weight initiator composition. The metallic alloy comprised of approximately 69.3 percent by weight silver, 17.9 percent by weight tin, 11.8 percent by weight copper and 0.9 percent by weight zinc, sold commercially as Optalloy™ by Dentsply International, Inc. The initiator composition is 10 parts by weight of benzoyl peroxide, 0.2 parts by weight of copper acetylacetonate and 3.5 parts by weight of ascorbyl palmitate. Liquid D is 12.8 percent by weight PENTA, 30.34 percent by weight OEMA, 13.0 percent by weight HEMA, 26.16 percent by weight TEGDMA, 14.0 percent by weight BisGMA, 3.628 percent by weight water (H₂O) and 0.067 percent by weight BHT. The powder-liquid mixture formed polymerizes to form a polymeric material having a flexural strength of 87.6 MPa and a flexural modulus of 10,393 MPa.

EXAMPLE 22

Powder E and liquid F are mixed in a ratio of 6.5 to 1 as shown in Table 1. Powder E is made by mixing 50 parts by weight silver/tin alloy (silver/tin 4/1 parts by weight), 50 parts by weight silanated barium boro alumino fluoride silicate glass and 1 part by weight initiator composition. The initiator composition is 10 parts by weight of benzoyl peroxide, 0.2 parts by weight of copper acetylacetonate and 3.5 parts by weight of ascorbyl palmitate. Liquid F is 45.08 percent by weight OEMA, 5.6 percent by weight H₂O, 30.0 percent by weight TEGDMA and 19.32 percent by weight HEMA.

The powder-liquid mixture formed polymerizes to form a polymeric material having a compressive strength of 225 MPa, a flexural strength of 56 MPa and a flexural modulus of 7,705 MPa.

EXAMPLE 23

Powder C and liquid F are mixed in a ratio of 6.5 to 1, as shown in Table 1. Powder C is made by mixing 50 parts by weight of a mixture of a metallic dental alloy powder, 50 parts barium boro alumino fluoride silicate glass and 1 part by weight initiator composition. The dental alloy has approximate composition of 69.3 percent by weight silver, 17.9 percent by weight tin, 1.8 percent by weight copper and 0.9 percent by weight zinc, sold commercially as Dispersalloy™ by Dentsply International, Inc. The initiator composition is 10 parts by weight of benzoyl peroxide, 0.2 parts by weight of copper acetylacetonate and 3.5 parts by weight of ascorbyl palmitate. Liquid F is 45.08 percent by weight OEMA, 5.6 percent by weight H₂O, 30.0 percent by weight TEGDMA and 19.32 percent by weight HEMA. The powder-liquid mixture formed polymerizes to form a polymeric material having a compressive strength of 200 MPa, a flexural strength of 60 MPa and a flexural modulus of 8,568 MPa.

EXAMPLE 24

Powder F and liquid F are mixed in a ratio of 6.5 to 1, as shown in Table 1. The powder is made by mixing 50 parts by weight alloy powder and 50 parts by weight silanated barium boro alumino fluoride silicate glass and 1 part by weight initiator composition. The alloy powder has an approximate composition of 56.7 percent by weight silver, 28.6 percent by weight tin and 14.7 percent by weight copper alloy—all spherical particles sold by Dentsply International Inc. as Unison™. The initiator composition is 10 parts by weight of benzoyl peroxide, 0.2 parts by weight of copper acetylacetonate and 3.5 parts by weight of ascorbyl palmitate. Liquid F is 45.08 percent by weight OEMA, 5.6 percent by weight H₂O, 30.0 percent by weight TEGDMA and 19.32 percent by weight HEMA. The powder-liquid mixture formed polymerizes to form a polymeric material having a compressive strength of 207 MPa, a flexural strength of 43.4 MPa and a flexural modulus of 6,548 MPa.

EXAMPLE 25

Powder E and liquid G are mixed in a ratio of 6.5 to 1, as shown in Table 1. The powder is made by mixing 50 parts by weight of a silver/tin alloy (silver/tin 4/1 parts by weight), 50 parts by weight percent silanated barium boro alumino fluoride silicate glass and 1 part by weight initiator composition. The initiator composition is 10 parts by weight of benzoyl peroxide, 0.2 parts by weight of copper acetylacetonate and 3.5 parts by weight of ascorbyl palmitate. Liquid G is 64.4 percent by weight 6-FDMA/GMA, 30.0 percent by weight TEGDMA and 5.6 percent by weight $H_2O$. The powder-liquid mixture polymerizes to form a polymeric material having a compressive strength of 192 MPa, a flexural strength of 40 MPa and a flexural modulus of 7,698 MPa.

EXAMPLE 26

Powder C and liquid G are mixed in a ratio of 6.5 to 1, as shown in Table 1. Powder C is made by mixing 50 parts by weight of a metallic dental alloy powder and 50 parts by weight barium boro alumino fluoride silicate glass and 1 part by weight initiator composition. The alloy has an approximate composition of is 69.3 percent by weight silver, 17.9 percent by weight tin, 11.8 percent by weight copper and 0.9 percent by weight zinc, sold commercially as Dispersalloy™ by Dentsply international, Inc. The initiator composition is 10 parts by weight of benzoyl peroxide, 0.2 parts by weight of copper acetylacetonate and 3.5 parts by weight of ascorbyl palmitate. Liquid G is 64.4 percent by weight 6-FDMA/GMA, 30.0 percent by weight TEGDMA and 5.6 percent by weight $H_2O$. The powder-liquid mixture polymerizes to form a polymeric material having a compressive strength of 190 MPa, a flexural strength of 50 MPa and a flexural modulus of 9,794 MPa.

EXAMPLE 27

Powder F and a liquid G are mixed in a ratio of 6.5 to 1, as shown in Table 1. Powder F is made by mixing 50 parts by weight Unison (56.7 percent by weight silver/28.6 percent by weight tin/14.7 percent by weight copper alloy—all spherical particles) and 50 parts by weight silanated barium boro alumino fluoride silicate glass and 1 part by weight initiator composition. The initiator composition is 10 parts by weight of benzoyl peroxide, 0.2 parts by weight of copper acetylacetonate and 3.5 parts by weight of ascorbyl palmitate. Liquid G is 64.4 percent by weight 6-FDMA/GMA, 30.0 percent by weight TEGDMA and 5.6 percent by weight $H_2O$. The powder-liquid mixture formed polymerizes to form a polymeric material having a compressive strength of 188 MPa, a flexural strength of 33.5 MPa and a flexural modulus of 9,350 MPa.

EXAMPLE 27A

Powder G and liquid H are mixed in a ratio of 3.8 to 1, as shown in Table 1. Powder G is made by mixing 50 parts by weight of silver powder, 50 parts by weight of silanated barium boro alumino fluoride silicate glass, 2 parts by weight stannous fluoride, and 1 part by weight of initiator composition. The initiator composition is 10 parts by weight of benzoyl peroxide, 0.6 parts by weight of copper acetylacetonate and 3.0 parts by weight of ascorbyl palmitate. The liquid is 37.03 percent by weight OEMA, 15.87 percent by weight HEMA, 24.8 percent by weight TEGDMA, 0.1 percent by weight BHT, 3.7 percent by weight $H_2O$ and 18.5 percent by weight PENTA. The liquid H is sealed in a pillow of polyethylene film to form a filled pillow. The filled pillow and powder G are enclosed in a plastic capsule, such as an IRM capsule, sold by Dentsply International Inc., L. D. Caulk Division. The pillow is ruptured by twisting the cap of the capsule, allowing the liquid H to conact powder G. The capsule is then placed in an actuator, and the actuator is operated for 8 seconds to mix the powder G and liquid H. During the actuation a paste is formed. The paste self cures to form a set polymeric material having a flexural strength of 128 MPa; a flexural modulus of 17,962 MPa, compressive strength of 207 MPa, and adhesion to dentin without priming of 958 psi.

EXAMPLE 27B

Powder H and Liquid I are mixed in a ratio of 4 to 1 as shown in Table 1 and as described in Example 1. Powder H is made by mixing 10 parts by weight silanated strontium alumino fluorosilicate glass, 10 parts by weight aluminum powder, 0.5 parts stannous fluoride, and 0.3 parts by weight of initiator. The initiator is made by mixing 10 parts by weight benzoyl peroxide (BPO), 0.2 parts by weight of cupric acetylacetonate and 3.5 parts by weight ascorbyl palmitate. Liquid I comprises 37.9 parts by weight OEMA, 4.5 parts by weight water, 25.2 parts by weight TEGDMA, 16.3 parts by weight HEMA, 0.1 percent by weight butylated hydroxytoluene, and 16.0 percent by weight PENTA. The powder-liquid mixture formed polymerizes to a polymeric material having a flexural strength of 72.1 MPa and a flexural modulus of 7392 MPa.

EXAMPLE 27C

Powder I and liquid H are mixed in a ratio of 10 to 1, as shown in Table 1. Powder I is made by mixing 9 parts by weight of stainless steel powder, 2 parts by weight of silanated barium boro alumino fluoride silicate glass, and 1 part by weight initiator composition. The initiator composition is 10 parts by weight benzoyl peroxide, 0.2 parts by weight of cupric acetylacetonate and 1.5 parts by weight of ascorbyl palmitate. The liquid is 37.03 percent by weight OEMA, 15.87 percent by weight HEMA, 24.8 percent by weight TEGDMA, 0.1 percent by weight BHT, 3.7 percent by weight $H_2O$ and 18.5 percent by weight PENTA. The liquid H is sealed in a pillow of polyethylene film to form a filled pillow. The filled pillow and powder I are enclosed in a plastic capsule, such as an IRM capsule, sold by Dentsply International Inc., L. D. Caulk Division. The pillow is ruptered by twisting the cape of the capsule, allowing the liquid H to conact powder I. The capsule is then placed in an actuator, and the actuator is operated for 4 seconds to mix the powder I and liquid H. During the actuation a paste is formed. The powder-liquid mixture polymerizes to form a polymeric material having a flexural strength of 93 Mpa and flexural modulus of 17,922 MPa.

Comparative Example

Polymerizable composite material (DYRACT light curable polymerizable paste sold by Dentsply International Inc.) which includes 28 percent monomer, 72 percent powder, and polymerizes to form polymeric material, polymerizes having a compressive strength of 245 MPa, a flexural strength of 97 MPa, a flexural modulus of 7,428 MPa, adhesion to dentin without priming of 391 psi, adhesion to dentin with priming using Prime and Bond (™) primer/adhesive sold by Dentsply International Inc., of 1682 psi and a wear of 178 using the same conditions and sample size as in the in vitro wear test described in Example 16.

TABLE 1

| EXAMPLE | SELF CURE P/L POWDER (TABLE 2) TO LIQUID (TABLE 3) RATIO | Compressive Strength (MPa) | Flexural Strength (MPa) | Flexural Modulus (MPa) | Adhesive bond strength to dentin (psi) B.S. w/o primer | BS *with primer | WEAR (average relative wear loss) |
|---|---|---|---|---|---|---|---|
| 16 | A/A (6.5/1) | 228 | 109 | 11,134 | 792 | 1272 | 37.1 |
| 17 | B/A (6.5/1) | 81 | 22 | 3,885 | — | — | |
| 18 | C/A (6.5/1) | 246 | 98 | 14,810 | 697 | 1426 | |
| 19 | J/A (7.0/1) | 214 | 80.1 | 10,833 | — | — | |
| 20 | C/B (6.5/1) | — | 49 | 6,562 | — | — | |
| 21 | D/D (6.5/1) | — | 87.6 | 10,393 | — | — | |
| 22 | E/F (6.5/1) | 225 | 56 | 7,705 | — | — | |
| 23 | C/F (6.5/1) | 200 | 60 | 8,568 | — | — | |
| 24 | F/F (6.5/1) | 207 | 43.4 | 6,548 | — | — | |
| 25 | E/G (6.5/1) | 192 | 40 | 7,698 | — | — | |
| 26 | C/G (6.5/1) | 190 | 50 | 9,794 | — | — | |
| 27 | F/G (6.5/1) | 188 | 33.5 | 9,350 | — | — | |
| Comparative 27A | G/H (3.8/1) | 245 207 | 97 128 | 7,428 17,962 | 391 958 | 1682 | 178 |
| 27B | H/I (4.0/1) | | 72.1 | 7,392 | | | |
| 27C | I/H (10/1) | | 93 | 17,922 | | | |

*Prime and Bond (TM) Primer used.

TABLE 2

| POWDER | | PARTS BY WEIGHT |
|---|---|---|
| A | Dispersalloy ™ (as shown in powder C below) | 20.5 |
| | SnF₂ | 0.6 |
| | Barium boro alumino silicate glass | 20.5 |
| | Initiator Composition (1) | 0.4 |
| B | Ag powder | 7.8 |
| | Barium Boro Alumino silicate glass | 7.8 |
| | Initiator Composition (1) | 0.08 |
| C | Dispersalloy ™ (69.3 silver/11.8 copper/17.9 tin/0.9 zinc) | 50 |
| | Barium Boro Alumino Fluorosilicate glass | 50 |
| | Initiator Composition (1) | 1 |
| D | Optaloy ™ (69.7 Silver/17.5 tin/11.8 copper/1.0 zinc alloy) | 50 |
| | Barium boro alumino silicate glass | 50 |
| | Initiator Composition (1) | 1 |
| E | Silver/tin alloy (4 parts/1 part by weight) | 50 |
| | Silanated Barium Boro Alumino Fluorosilicate glass | 50 |
| | Initiator Composition (1) | 1 |
| F | Unison (56.7 Silver/28.6 tin/14.7 copper alloy) | 50 |
| | Silanated Barium Boro Alumino Fluorosilicate glass | 50 |
| | Initiator Composition (1) | 1 |
| G | Silver powder | 50 |
| | silanated barium boro alumino fluorosilicate glass | 50 |
| | stannous fluoride | 2 |
| | Initiator Composition (2) | 1 |
| H | Silanated Strontium alumino fluorosilicate glass | 10 |
| | Aluminum powder | 10 |
| | Stannous fluoride | 0.5 |
| | Initiator Composition (1) | 0.3 |
| I | Stainless steel powder | 9.0 |
| | Silanated Barium boro alumino fluorosilicate glass | 2.0 |
| | Initiator Composition (3) | 1.0 |
| J | Dispersalloy (as shown in powder C) | 10 |
| | Silanated Barium boro Alumino Fluorosilicate glass | 4 |
| | Initiator Composition (1) | 0.1 |

(1) Initiator Composition
10 parts benzoyl peroxide
0.2 parts copper acetylacetonate
3.5 parts ascorbyl palmitate (2) Initiator Composition
10 parts benzoyl peroxide
0.6 parts copper acetylacetonate
3.0 parts ascorbyl palmitate (3) Initiator Composition
10 parts benzoyl peroxide
0.2 parts copper acetylacetonate
1.5 parts ascorbyl palmitate

TABLE 3

| LIQUID | | PERCENT BY WEIGHT |
|---|---|---|
| A | Penta | 16.0 |
| | OEMA | 37.926 |
| | HEMA | 16.254 |
| | TEGDMA | 25.20 |
| | $H_2O$ | 4.536 |
| | BHT | 0.084 |
| B | Compound VIIIA | 35.6 |
| | TEGDMA | 35.6 |
| | HEMA | 23.9 |
| | $H_2O$ | 4.9 |
| C | OEMA | 44.8 |
| | TEGDMA | 30.0 |
| | $H_2O$ | 4.1 |
| | HEMA | 19.4 |
| D | Penta | 12.8 |
| | OEMA | 30.34 |
| | HEMA | 13.0 |
| | TEGDMA | 26.16 |

TABLE 3-continued

| LIQUID | | PERCENT BY WEIGHT |
|---|---|---|
| | PENTA | 16.0 |
| | BHT | 0.1 |

EXAMPLE 28

Compound VIIIA is formed in a 500 mL round bottom flask by placing therein 15.5 g ODPA (0.05 mole), 3.45 g 1,3-benzenedimethanol (0.025 mole), 0.74 g 4-pyrrolidinopyridine (0.005 mole) and 5.05 g triethylamine (TEA) (0.05 mole) in 300 mL methylene chloride. On addition of TEA, the solids dissolved. After two hours stirring at room temperature, 6.5 g HEMA (0.05 mole), 0.74 g 4-pyrrolidinopyridine (0.005 mole) and 5.05 g TEA (0.05 mole) are added. After stirring an additional two hours at room temperature, the solution is washed twice with 2N hydrochloric acid and twice with deionized water. The solution is dried over anhydrous sodium sulfate and the solvent stripped under reduced pressure to give a light yellow resin. Compound VIIIA has the structural formula:

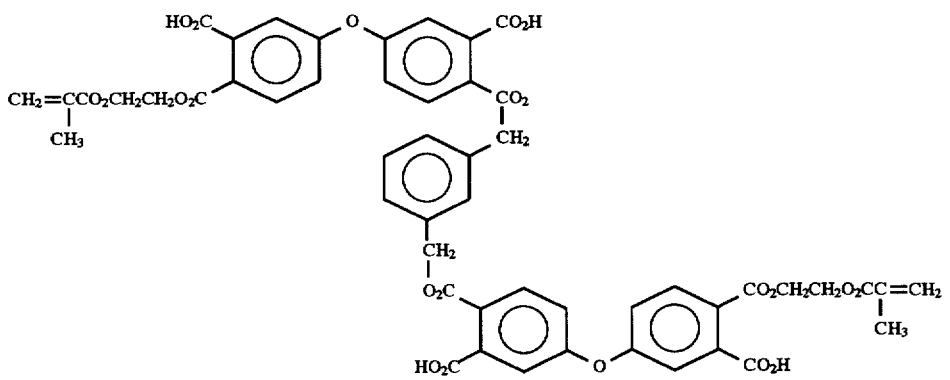

VIII A

TABLE 3-continued

| LIQUID | | PERCENT BY WEIGHT |
|---|---|---|
| | BisGMA | 14.0 |
| | $H_2O$ | 3.628 |
| | BHT | 0.067 |
| E | TEGDMA | 30 |
| (VLC) | OEMA | 44.8 |
| | HEMA | 19.2 |
| | $H_2O$ | 4.1 |
| | BHT | 0.1 |
| | CQ | 0.2 |
| | EDAB | 0.6 |
| | Uvinol/M-40 | 1.0 |
| F | OEMA | 45.08 |
| | $H_2O$ | 5.6 |
| | TEGDMA | 30.0 |
| | HEMA | 19.32 |
| G | 6-FDMA/GMA | 64.4 |
| | TEGDMA | 30.0 |
| | $H_2O$ | 5.6 |
| H | OEMA | 37.03 |
| | HEMA | 15.87 |
| | PENTA | 18.5 |
| | TEGDMA | 24.8 |
| | $H_2O$ | 3.7 |
| | BHT | 0.1 |
| I | OEMA | 37.9 |
| | Water | 4.5 |
| | TEGDMA | 25.2 |
| | HEMA | 16.3 |

EXAMPLE 28A

Compound VIIIB is formed in a 500 mL round bottom flask by placing therein 15.5 g ODPA (0.05 mole), 3.45 g 1,4-benzenedimethanol (0.025 mole), 0.74 g pyrrolidinopyridine (0.005 mole) and 5.05 g triethylamine (TEA) (0.05 mole) in 300 mL methylene chloride. On addition of TEA, the solids dissolved. After two hours stirring at room temperature, 6.5 g HEMA (0.05 mole), 0.74 g 4-pyrrolidinopyridine (0.005 mole) and 5.05 g TEA (0.05 mole) are added. After an additional two hours stirring at room temperature, the solution is washed twice with 2N hydrochloric acid and twice with deionized water. The solution is dried over anhydrous sodium sulfate and the solvent stripped under reduced pressure to give a light yellow resin. Compound VIIIB has the structural formula:

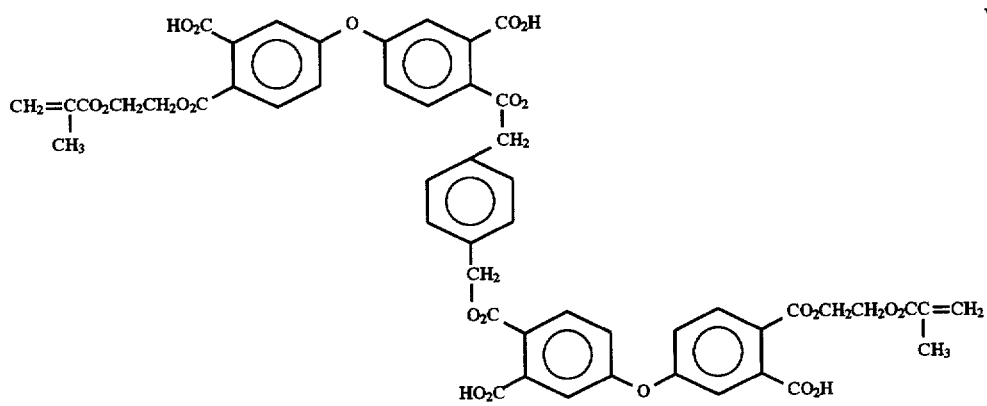

VIII B

EXAMPLE 28B

Compound VIIIC is formed in a 500 mL round bottom flask by placing therein 15.5 g ODPA (0.05 mole), 11.1 grams ethoxylated bisphenol A (0.027 mole), 0.74 g 4-pyrrolidinopyridine (0.005 mole) and 5.05 g triethylamine (TEA) (0.05 mole) in 300 mL methylene chloride. On addition of TEA, the solids dissolved. After two hours stirring at room temperature, 6.5 g HEMA (0.05 mole), 0.74 g 4-pyrrolidinopyridine (0.005 mole) and 5.05 g TEA (0.05 mole) are added. After stirring at room temperature overnight, the solution was treated with 200 ml of 2N hydrochloric acid and 200 ml of methylene chloride. The layers were separated and the methylene chloride solution was washed twice with deionized water. The solution was dried over anhydrous sodium sulfate and the solvent stripped under reduced pressure to give a viscous yellow resin. Compound VIIIC has the structural formula:

TABLE 4

RESTORATIVE COMPOSITIONS

| | Example 29 | Example 30 | Example 31 |
|---|---|---|---|
| POWDER | | | |
| Dispersalloy | 49.5 | 49.5 | 49.5 |
| Silanated Barium boro alumino fluorosilicate glass | 49.5 | 49.5 | 49.5 |
| Initiator | 1.0 | 1.0 | 1.0 |
| LIQUID | | | |
| OEMA | 45.15 | — | — |
| HEMA | 19.35 | — | 23.9 |
| TEGDMA | 30.00 | 50.0 | 35.6 |
| WATER | 5.40 | — | 4.9 |

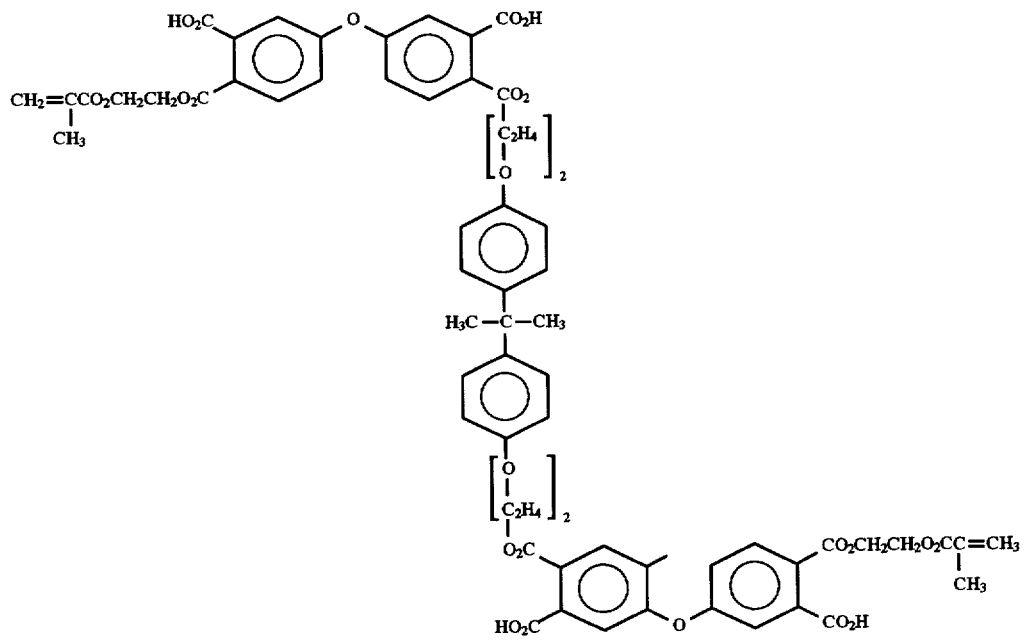

VIII C

TABLE 4-continued

RESTORATIVE COMPOSITIONS

|  | Example 29 | Example 30 | Example 31 |
|---|---|---|---|
| BHT | 0.10 | — | |
| Compound VIII A | — | 50.0 | 35.6 |
| Flexural Strength, MPa | 60 | 87.6 | 49 |
| Flexural Modulus, MPa | 8568 | 8488 | 6562 |

TABLE 5

CEMENT COMPOSITIONS

|  | Example 32 | Example 33 | Example 33A |
|---|---|---|---|
| POWDER | | | |
| Strontium alumino flurosilicate glass | 98.83 | 98.83 | 98.83 |
| Benzoyl peroxide | 1.0 | 1.0 | 1.0 |
| Copper acetyl acetonate | 0.02 | 0.02 | 0.02 |
| Ascorbyl palmitate | 0.15 | 0.15 | 0.15 |
| LIQUID | | | |
| Compound VIIIB | 56.2 | 56.2 | |
| Compound VIIIC | | | 62.3 |
| HEMA | 36.4 | 35.4 | 15.7 |
| H$_2$O | 7.4 | 7.4 | |
| Lucerin TPO | | 1.0 | 6.0 |
| TEGDMA | | | 16.0 |
| Bond strength to dentin without primer (psi) | 587 | 975* | 800 |

*Visible light cured

EXAMPLE 29

A powder and a liquid are mixed in a ratio of 6 to 1 as shown in Table 4. The powder is 49.5 percent by weight of a mixture of 49.5 percent by weight silanated barium boro alumino fluoride silicate glass and 1.0 percent by weight initiator. The mixture of alloy is 69.3 percent by weight silver, 17.9 percent by weight tin, 11.8 percent by weight copper and 0.9 percent by weight zinc, sold commercially as Dispersalloy™ by Dentsply International, Inc. The initiator composition is the same as is used in Example 27. The liquid is 45.15 percent by weight OEMA, 19.35 percent by weight HEMA, 30.00 percent by weight TEGDMA, 5.40 percent by weight water and 0.10 percent by weight BHT. The composition is polymerized to form polymeric material having a flexural strength of 60 MPa and a flexural modulus of 8568 MPa as shown in Table 4.

EXAMPLE 30

A powder and a liquid are mixed in a ratio of 6 to 1 as shown in Table 4. The powder is 49.5 percent by weight of a mixture of 49.5 percent by weight silanated barium boro alumino fluoride silicate glass and 1.0 percent by weight initiator. The mixture of alloy is 69.3 percent by weight silver, 17.9 percent by weight tin, 11.8 percent by weight copper and 0.9 percent by weight zinc, sold commercially as Dispersalloy™ by Dentsply international, Inc. The initiator composition is the same as is used in Example 27. The liquid is 50 percent by weight TEGDMA and 50 percent by weight Compound VIIIA made as described in Example 28. The composition is polymerized to form polymeric material having a flexural strength o 87.6 MPa and a flexural modulus of 8488 MPa as shown in Table 4.

EXAMPLE 31

A powder and a liquid are mixed in a ratio of 6 to 1 as shown in Table 4. The powder is 49.5 percent by weight of

TABLE 6

COMPOSITE RESTORATIVES

|  | Example 34 | Example 35 | Example 36 | Example 37 | Example 38 | Example 39 | Example 39A |
|---|---|---|---|---|---|---|---|
| Silanated Barium boro alumino silicate glass | 73.79 | 76.82 | 70.79 | 73.89 | 75.50 | 76.85 | 76.85 |
| CQ | 0.05 | 0.05 | 0.05 | 0.05 | 0.05 | 0.04 | 0.04 |
| EDAB | 0.21 | 0.19 | 0.20 | 0.18 | 0.18 | 0.16 | 0.16 |
| TEGDMA | 7.82 | 8.02 | 8.69 | 3.09 | 4.83 | 7.68 | 7.68 |
| E-U Resin* | — | — | — | 15.58 | 12.20 | — | — |
| EBPADMA** | — | — | — | — | — | 7.59 | 7.59 |
| Compound VIII A | 18.13 | — | — | — | — | — | — |
| Compound VIII C | — | 14.92 | 20.27 | 7.21 | 7.24 | 7.68 | — |
| OEMAMA | — | — | — | — | — | — | 7.68 |
| Transverse Strength (MPa) | 64.7 | 67.7 | 58.3 | 137.9 | 134.6 | 110.6 | |
| Flexural Modulus (MPa) | 11466 | 14379 | 9294 | 11149 | 11368 | 11600 | |
| Diametral Tensile Strength (MPa) | 43.8 | 31.7 | 22.5 | 49.1 | 47.6 | 47.7 | |
| Compressive Strength (MPa) | 200 | 194 | 169 | 251 | 246 | 227 | |
| Wear (average relative wear loss) | — | | | 16.9 | 13.5 | | |

*E-U resin referred to in Table 6 and Examples 37 and 38 is the reaction product of bis phenol A glycidyl dimethacrylate and hexamethylene diisocyanate in a 5 to 4 equivalence ratio, with triethylene glycol dimethacrylate and ethoxylated bisphenol A as diluents and/or coreactants.

**EBPADMA referred to in Table 6 and Examples 39 and 39A is ethoxylated bis phenol A dimethacrylate a mixture of spherical and cut alloy, 49.5 percent by weight silanated barium boro alumino fluoride silicate glass and 1.0 percent by weight initiator. The mixture of alloy is 69.3 percent by weight silver, 17.9 percent by weight tin, 11.8 percent by weight copper and 0.9 percent by weight zinc, sold commercially as DisPersalloy™ by Dentsply International, Inc. The initiator composition is the same as is used in Example 27. The liquid is 23.9 percent by weight HEMA, 35.6 percent by weight TEGDMA, 4.9 percent by weight water (H₂O) and 35.6 percent by weight Compound VIIIA made as discussed in Example 28.

The composition is polymerized to form polymeric material having a flexural strength of 49 MPa and a flexural modulus of 6562 MPa as shown in Table 4.

EXAMPLE 32

A powder and a liquid are mixed in a ratio of 2 to 1 and have the compositions as shown in Table 5. The powder is 98.83 percent by weight strontium alumino fluorosilicate glass, 1.0 percent by weight benzoyl peroxide, 0.02 percent by weight copper acetylacetonate and 0.15 percent by weight ascorbyl palmitate. The liquid is 36.4 percent by weight HEMA, 7.4 percent by weight water (H₂O) and 56.2 percent by weight compound VIIIB, formed as disclosed in Example 28A. The composition is polymerized to form polymeric material having a bond strength to dentin of 587 psi as shown in Table 5.

EXAMPLE 33

A powder and a liquid are mixed in a ratio of 2 to 1 and have the compositions shown in Table 5. The powder is 98.83 strontium alumino fluorosilicate glass, 1.0 percent by weight benzoyl peroxide, 0.02 percent by weight copper acetylacetonate and 0.15 percent by weight ascorbyl palmitate. The liquid is 35.4 percent by weight HEMA, 7.4 percent by weight water (H₂O), 56.2 percent by weight compound VIIIB formed as disclosed in Example 28A and 1.0 percent by weight Lucerin TPO (2,4,6,-trimethyl benzoyl diphenyl phosphine oxide) photoinitiator. The composition is polymerized using visible light to form a polymeric material having a bond strength of 800 psi and shown in Table 5.

EXAMPLE 33A

A powder and a liquid are mixed in a ratio of 2 to 1 as shown in Table 5. The powder is 98.83 strontium alumino fluorosilicate glass, 1.0 percent by weight benzoyl peroxide, 0.02 percent by weight copper acetylacetonate and 0.15 percent by weight ascorbyl palmitate. The liquid is 15.7 percent by weight HEMA, 16 percent by weight TEGDMA, 6 percent by weight water (H₂O) and 62.3 percent by weight compound VIIIC (made as disclosed in Example 28B). The composition is polymerized to form polymeric material having a bond strength of 800 psi as shown in Table 5.

EXAMPLE 34

A powder and a liquid are mixed as shown in Table 6. The powder is 73.79 percent by weight of the composition and is silanated barium boroalumino silicate glass powder, 7.82 percent by weight is TEGDMA, 18.13 percent by weight is compound VIIIA (made as disclosed in Example 28), 0.21 percent by weight is EDAB and 0.05 percent by weight is camphorquinone. The composition is exposed to visible light from a light curing unit for 40 seconds and polymerizes to form polymeric material having a transverse strength of 64.7 MPa, a flexural modulus of 11466 MPa, a diametral tensile strength of 43.8 MPa and a compressive strength of 200 psi as shown in Table 6.

EXAMPLE 35

A powder and a liquid are mixed as shown in Table 6. The powder is 76.82 percent by weight of the composition and is silanated barium boro alumino silicate glass powder, 0.05 percent by weight of the composition is camphorquinone, 0.19 percent by weight of the composition is EDAB, 8.02 percent by weight of the composition is TEGDMA and 14.92 percent by weight of the composition is Compound VIIIC made as disclosed in Example 28B. The composition is exposed to visible light from a light curing unit for 40 seconds and polymerizes to form polymeric material having a transverse strength of 67.7 MPa, a flexural modulus of 14379 MPa, a diametral tensile strength of 31.7 MPa and a compressive strength of 194 as shown in Table 6.

EXAMPLE 36

A powder and a liquid are mixed as shown in Table 6. The powder is 70.79 percent by weight of the composition and is silanated barium boro alumino silicate glass powder, 0.05 percent of the composition is camphorquinone, 0.20 percent by weight of the composition is EDAB, 8.69 percent by weight of the composition is TEGDMA, 20.27 percent by weight of the composition is Compound VIIIB made as disclosed in Example 28B. The composition is exposed to visible light from a light curing unit for 40 seconds and polymerizes to form polymeric material having a transverse strength of 58.3 MPa, a flexural modulus of 9294 MPa, a diametral tensile strength of 22.5 MPa and a compressive strength of 169 MPa as shown in Table 6.

EXAMPLE 37

A powder and a liquid are mixed as shown in Table 6. The powder is 73.89 percent by weight of the composition and is silanated barium boro alumino silicate glass powder, 0.05 percent of the composition is camphorquinone, 0.18 percent by weight of the composition is EDAB, 3.09 percent by weight of the composition is TEGDMA, 15.58 percent by weight of the composition is "E-U resin" which is the reaction product of bis phenol A dimethacrylate and hexamethylene diisocyanate in a 5 to 4 equivalence ratio, with triethylene glycol dimethacrylate and ethoxylated bisphenol A as diluents and/or coreactants, 7.21 percent by weight of the composition is Compound VIIIC made as disclosed in Example 28B. The composition is exposed to visible light from a light curing unit for 40 seconds and polymerizes to form polymeric material having a transverse strength of 137.9 MPa, a flexural modulus of 11149 MPa, a diametral tensile strength of 49.1 MPa, a compressive strength of 251 MPa and wear of 16.9 as shown in Table 6 using the same conditions and sample size as in the in vitro wear test discussed in Example 18.

EXAMPLE 38

A powder and a liquid are mixed as shown in Table 6. The powder is 75.50 percent by weight of the composition is light yellow gray silanated barium boro aluminosilicate glass powder, 0.05 percent by weight of the composition is camphorquinone, 0.18 percent by weight of the composition is EDAB, 4.83 percent by weight of the composition is TEGDMA, 12.20 percent by weight of the composition is E-U Resin and 7.24 percent by weight of the composition is Compound VIIIC made as disclosed in Example 28B. The composition is exposed to visible light from a light curing unit for 40 seconds and polymerizes to form polymeric material having a transverse strength of 134.6 MPa, a flexural modulus of 11368 MPa, a diametral tensile strength of 47.6 MPa, a compressive strength of 246 MPa and wear of 13.5 as shown in Table 6.

EXAMPLE 39

A powder and a liquid are mixed as shown in Table 6. The powder which is 76.85 percent by weight of the composition is light yellow gray silanated barium boro alumino silicate glass powder. 0.04 percent by weight of the composition is camphorquinone, 0.16 percent by weight of the composition is EDAB, 7.68 percent by weight of the composition is TEGDMA and 7.59 percent by weight of the composition is EBPADMA, 7.68 percent by weight of the composition is Compound VIIIC and made as disclosed in Example 28B. The composition is exposed to visible light from a light curing unit 40 seconds and polymerizes to form polymeric material having a transverse strength of 110.6 MPa, a flexural modulus of 11600 MPa, a diametral tensile strength of 47.7 MPa and a compressive strength of 227 MPa as shown in Table 6.

EXAMPLE 39A

A powder and a liquid are mixed as shown in Table 6. The powder which is 76.85 percent by weight of the composition is light yellow gray silanated barium boro alumino silicate glass powder. 0.04 percent by weight of the composition is camphorquinone, 0.16 percent by weight of the composition is EDAB, 7.68 percent by weight of the composition is TEGDMA and 7.59 percent by weight of the composition is EBPADMA, 7.68 percent by weight of the composition is OEMAMA and made as disclosed in Example A. The composition is exposed to visible light from a light curing unit 40 seconds and polymerizes to form polymeric material.

Products in accordance with a preferred embodiment of the invention are now described with more particular reference to FIGS. 1–5. As shown in FIG. 1, each part of multiple part compositions in accordance with a preferred embodiment of the invention is enclosed in a chamber of an enclosure. Generally at least one wall of at least one of the chambers is adapted to be ruptured or otherwise penetrated to allow the complete composition to be mixed. As shown in FIG. 1, each of parts 12 and 14 of a two part composition in accordance with a preferred embodiment of the invention is enclosed in a chamber of enclosure 10. The enclosure 10 has a wall 16 which is ruptured prior to or during mixing of the two part composition. The two part composition within enclosure 10 includes a polymerizable compound, polymerization initiator and at least 10 percent by weight of ceramic, metal and/or metal oxide filler particles having a particle size less than 500 microns.

Figure 2:
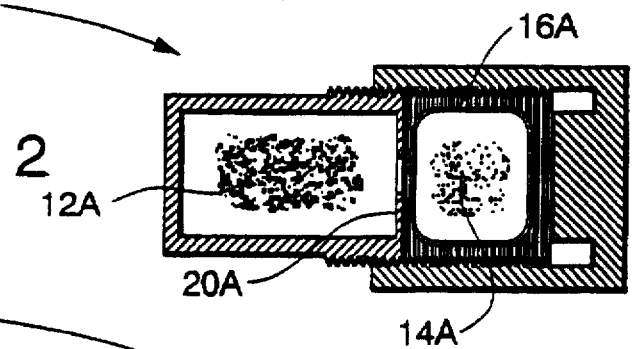
FIG. 2 is a schematic representation of two part composition in a storage and mixing enclosure having a rigid wall with an aperture therethrough in accordance with a preferred embodiment of the invention.

In accordance with a preferred embodiment of the invention shown in FIG. 2, wall 16A of enclosure 10A may be ruptured, for example by forcing wall 16A against a rigid wall 20A which has with an aperture therethrough. Upon being vibrated first and second parts 12A and 14A are mixed. Apart from the composition enclosed, such enclosures include those used for mixing temporary sealing material, such as for mixing eugenol and zinc oxide in a 1 to 4 weight ratio, for example IRM capsules, sold by L. D. Caulk.

Figure 3:
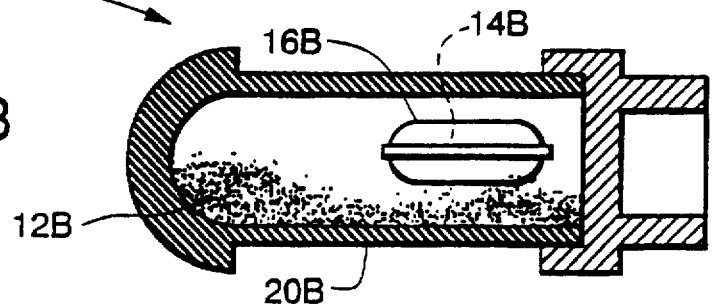
FIG. 3 is a schematic representation of two part composition in a storage and mixing enclosure enclosing a rupturable container in accordance with a preferred embodiment of the invention.
Figure 4:
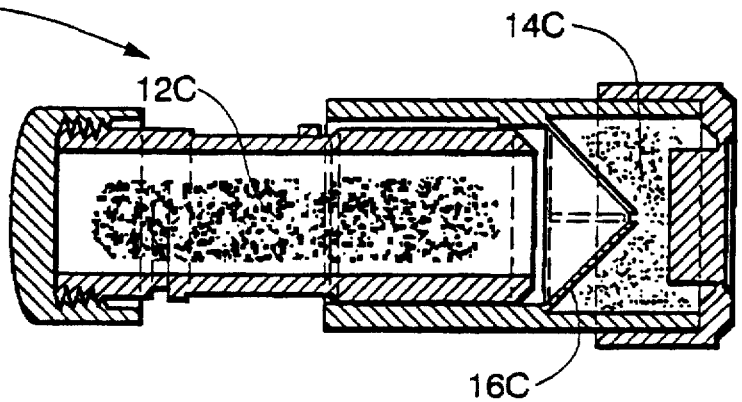
FIG. 4 is a schematic representation of two part composition in a storage and mixing enclosure having a rupturable wall in accordance with a preferred embodiment of the invention.

Alternatively, as shown in FIG. 3, the wall 16B of enclosure 10B may be ruptured by its impact against a rigid wall 20B. Upon being vibrated first and second parts 12A and 14A are mixed. Apart from the composition enclosed, such enclosures include those used for mixing mercury amalgam in a vibrational mixer for example as disclosed by Muhlbauer in U.S. Pat. Nos. 4,306,651 and 4,396,117. A further alternative embodiment of the invention as shown in FIG. 4 has wall 16C which may be ruptured, and the first and second compositions 12C and 14C in accordance with the invention which are mixed prior to being extruded from capsule enclosure 10C. Apart from the composition enclosed, such enclosures are disclosed by Welsh in U.S. Pat. No. 4,515,267.

Figure 5:
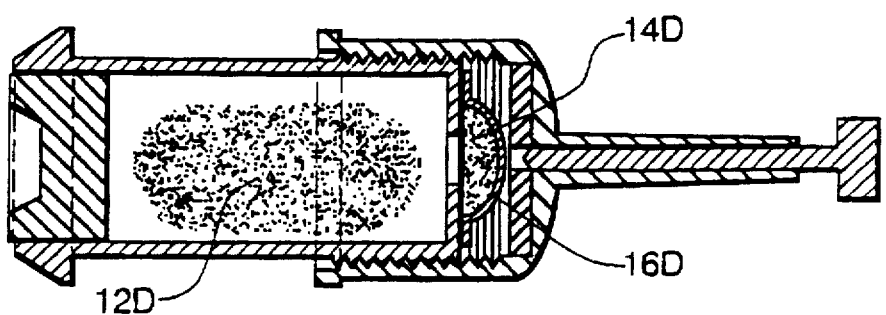
FIG. 5 is a schematic representation of two part composition in a storage and mixing enclosure having a rupturable wall in accordance with a preferred embodiment of the invention.

A further alternative embodiment of the invention as shown in FIG. 5 has wall 16D which may be ruptured, and the first and second compositions 12D and 14D in accordance with the invention which are mixed prior to being extruded from capsule enclosure 10D. Apart from the composition enclosed, such enclosures are disclosed by Green in U.S. Pat. No. 4,648,532 (RE 33 801).

It should be understood that while the present invention has been described in considerable detail with respect to certain specific embodiments thereof, it should not be considered limited to such embodiments but may be used in other ways without departure from the spirit of the invention and the scope of the appended claims.

What is claimed is:

1. A polymerizable dental composition, comprising:
   at least one compound within the scope of the general formula:

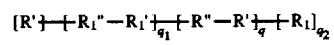

wherein each R' indepently is within the scope of the general formula:

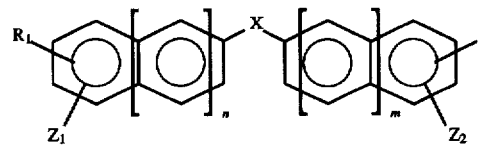

each $R_1'$ independently is within the scope of the general formula:

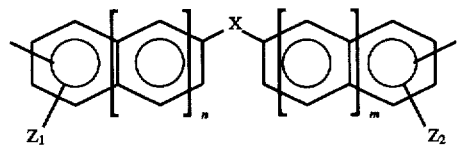

each $R_1''$ and R" independently is a divalent hydrocarbon group selected from the group consisting of alkylene having from 4 to 40 carbon atoms, aryl containing alkylene having from 6 to 40 carbon atoms, ether containing alkylene having from 2 to 40 carbons, alkyl aryl containing alkylene having from 7 to 40 carbon atoms and alkyl containing alkylenes having from 2 to 40 carbon atoms, each X independently is

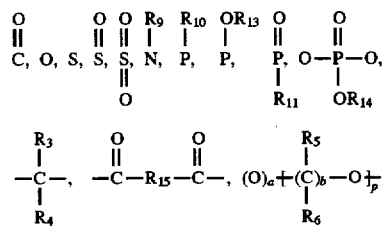

or omitted whereby the adjacent rings are directly covalently bonded together, each $R_1$ independently is a polymerizable unsaturated moiety having from 2 to 30 carbon atoms, $R_3$, $R_4$, $R_5$, and $R_6$ each independently is hydrogen, halogen, alkyl having from 1 to 10 carbon atoms or halogenated alkyl of from 1 to 10 carbon atoms, $R_9$, $R_{10}$, $R_{11}$, $R_{12}$, $R_{13}$ and $R_{14}$ each independently is hydrogen, alkyl having from 1 to 10 carbon atoms or aryl having from 6 to 10 carbon atoms, $R_{15}$ is alkylene diol, alkylene diamine, substituted alkylene diol or substituted alkylene diamine, $Z_1$ and $Z_2$ each independently is a moiety including an acid group, a, m and n each independently is 0 or 1, b, and p independently is an integer from 1 to 10, q is zero or 1, $q_1$ is zero, 1 or 2, $q_2$ is zero or 1, when q is zero; $q_2$ is 1; and when q is 1 $q_2$ is zero, an effective amount of a polymerization initiator, and at least 10 percent by weight of ceramic, metal and/or metal oxide filler particles having a particle size less than 500 microns.

2. The composition of claim 1 wherein q is 1 and $R_1$ has from 2 to 20 carbon atoms.

3. The composition of claim 1 wherein each $R_1$ independently is:

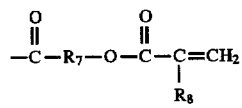

wherein $R_2$ is a divalent carbon containing radical and $R_8$ is hydrogen, halogen or alkyl having from 1 to 10 carbon atoms.

4. The composition of claim 3 wherein $R_7$ is a divalent carbon containing radical and $R_8$ is hydrogen, halogen or alkyl having from 1 to 10 carbon atoms.

5. The composition of claim 1 wherein R" is

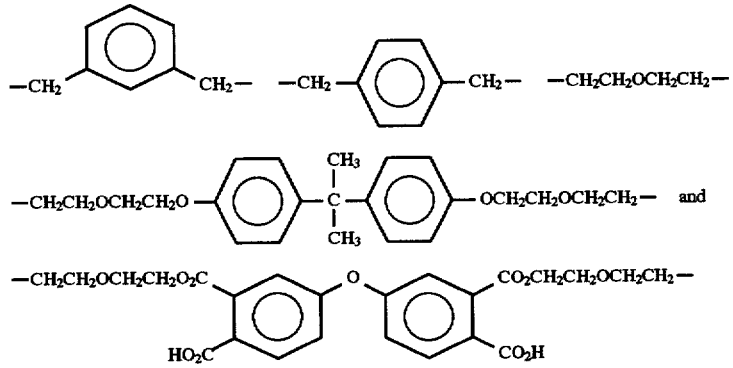

6. The composition of claim 1 wherein said composition comprises at least 50 percent by weight of said filler.

7. The composition of claim 1 wherein said composition comprises at least 80 percent by weight of said filler.

8. The composition of claim 1 further comprising fluoride releasing particles.

9. The composition of claim 1 further comprising glass particles, said glass particles comprising at least 10 percent by weight of said composition.

10. The composition of claim 1 wherein said particles comprise more than 95 percent by weight of composition.

11. The composition of claim 1 wherein said initiator is a photoinitiator or a redox initiator.

12. The composition of claim 1 wherein said composition is enclosed by a container.

13. The composition of claim 12 wherein said container comprises a wall adapted to be ruptured prior to removing said composition from said enclosure.

14. The composition of claim 13 wherein said wall comprises polymeric film or aluminum foil.

15. The composition of claim 13 wherein said wall comprises a nozzle.

16. The composition of claim 13 wherein said wall adapted to be ruptured is positioned adjacent to a rigid wall having an aperture therethrough.

17. A polymerizable compound within the scope of the general formula,

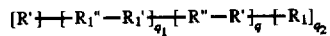

wherein each R' independently is within the scope of the general formula:

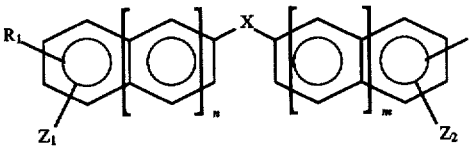

each $R_1'$ independently is within the scope of the general formula:

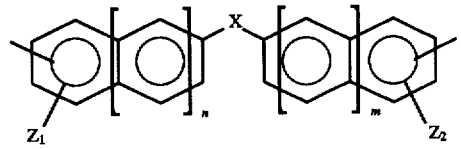

each $R_1''$ and R" independently is a divalent hydrocarbon group selected from the group consisting of alkylene having from 4 to 40 carbon atoms, aryl containing alkylene having from 6 to 40 carbon atoms, ether containing alkylene having from 2 to 40 carbons, alkyl aryl containing alkylene having from 7 to 40 carbon atoms and alkyl containing alkylenes having from 2 to 40 carbon atoms, each X independently is

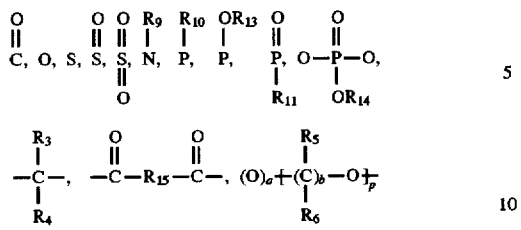

or omitted whereby the adjacent rings are directly covalently bonded together, each $R_1$ independently is a polymerizable unsaturated moiety having from 2 to 30 carbon atoms,

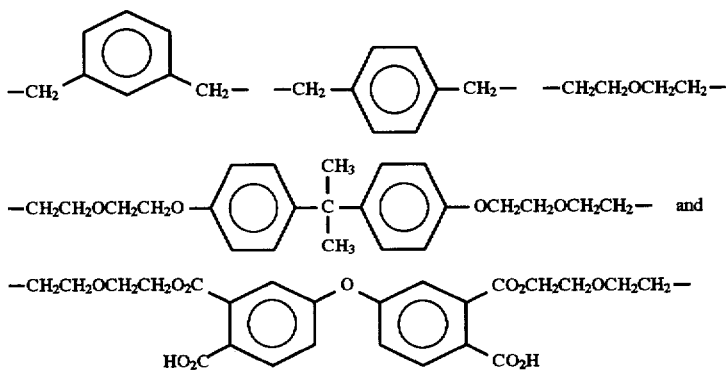

$R_3$, $R_4$, $R_5$, and $R_6$ each independently is hydrogen, halogen, alkyl having from 1 to 10 carbon atoms or halogenated alkyl of from 1 to 10 carbon atoms, $R_9$, $R_{10}$, $R_{11}$, $R_{12}$, $R_{13}$ and $R_{14}$ each independently is hydrogen, alkyl having from 1 to 10 carbon atoms or aryl having from 6 to 10 carbon atoms, $R_{15}$ is alkylene diol, alkylene diamine, substituted alkylene diol or substituted alkylene diamine, $Z_1$ and $Z_2$ each independently is a moiety including an acid group, a, m and n each independently is 0 or 1, b, and p independently is an integer from 1 to 10, at least one of q and $q_1$ is greater than zero, q is zero or 1, $q_1$ is zero, 1 or 2, $q_2$ is zero or 1, and when q is 1 $q_2$ is zero.

18. The compound of claim 17 wherein R" is

19. The compound of claim 17 in a composition comprising at least 10 percent by weight of filler particles and which adheres to dentin with an adhesive bond strength of at least 300 psi.

20. The compound of claim 19 wherein said filler comprises ceramic, metal, metal oxide or fluoride releasing particles.

21. The compound of claim 19 wherein said filler comprises at least 90 percent by weight of composition and at least 10 percent of said filler is metal or metal oxide.

22. The compound of claim 19 wherein said filler particles comprise more than 95 percent by weight of composition.

23. The compound of claim 17 wherein $R_{15}$ is

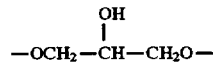

* * * * *

UNITED STATES PATENT AND TRADEMARK OFFICE
CERTIFICATE OF CORRECTION

PATENT NO. : 5,710,194
DATED : January 20, 1998
INVENTOR(S) : Paul D. Hammesfahr, Kewang Lu and Paul A. Silver It is certified that error appears in the above-indentified patent and that said Letters Patent is hereby corrected as shown below:

In claim 1, column 32, line 58 of the Patent after " 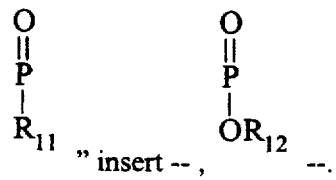 " insert -- , --.

In claim 17, column 35, line 5 of the Patent, after " 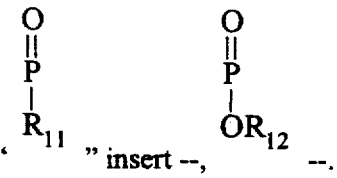 " insert --, --.

Signed and Sealed this

Eleventh Day of August 1998

Attest:

Attesting Officer

BRUCE LEHMAN

Commissioner of Patents and Trademarks